United States Patent [19]

Wilhelm et al.

[11] 4,075,335
[45] Feb. 21, 1978

[54] PHARMACEUTICAL PIPERIDINE DERIVATIVES

[75] Inventors: Max Wilhelm, Watchung, N.J.; Kurt Eichenberger, Therwil, Switzerland; Herbert Schroter, Fullinsdorf, Switzerland; Franz Ostermayer, Riehen, Switzerland

[73] Assignee: Ciba-Geigy Corporation, Ardsley, N.Y.

[21] Appl. No.: 652,966

[22] Filed: Jan. 28, 1976

Related U.S. Application Data

[60] Division of Ser. No. 483,742, June 27, 1974, Pat. No. 3,956,335, which is a continuation-in-part of Ser. No. 389,106, Aug. 16, 1973, abandoned.

[30] Foreign Application Priority Data

Apr. 30, 1974  Switzerland ............. 5907/74
Aug. 24, 1972  Switzerland ............. 12539/72
July 3, 1973   Switzerland ............. 9670/73

[51] Int. Cl.$^2$ .................................. A61K 31/33
[52] U.S. Cl. .................. 424/244; 424/246; 424/250; 424/251; 424/267; 424/273 R; 424/285; 424/317
[58] Field of Search ............. 424/246, 267, 274, 285, 424/244

[56] References Cited

U.S. PATENT DOCUMENTS 3,318,900  5/1967  Janssen ..................... 260/293.6
3,459,757  8/1969  Wright et al. .............. 260/293.7
3,956,335  5/1976  Wilhelm et al. ............ 424/267
3,969,518  7/1976  Novello ................... 424/246

Primary Examiner—V. D. Turner
Attorney, Agent, or Firm—John J. Maitner

[57] ABSTRACT

Piperidines of the formula

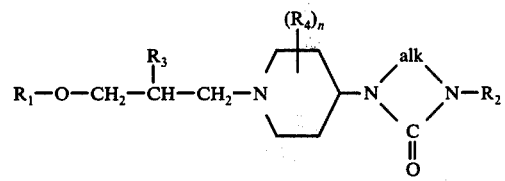

in which $R_1$ stands for optionally substituted aryl, $R_2$ for hydrogen, lower alkyl, lower alkenyl, acyl or α-aryl-lower alkyl, $R_3$ for a free or substituted hydroxyl group, alk for lower alkylene which separates the two nitrogen atoms by 2 or 3 carbon atoms, $R_4$ represents hydrogen or lower alkyl and $n$ represents an integer from 1 to 4, and their salts as well as processes for their manufacture and pharmaceutical compositions comprising such compounds, and a process for lowering the blood pressure wherein such compositions are administered to a warm-blooded host.

13 Claims, No Drawings

PHARMACEUTICAL PIPERIDINE DERIVATIVES

CROSS REFERENCE TO OTHER APPLICATIONS

This is a division of copending application Ser. No. 483,742, filed June 27, 1974, now U.S. Pat. No. 3,956,335 which, in turn, is a continuation in part of our copending application Ser. No. 389,106, filed Aug. 16, 1973, now abandoned.

SUMMARY OF THE INVENTION

The invention relates to new piperidines of the formula I

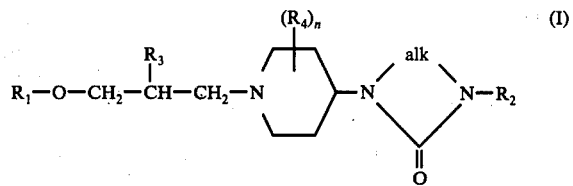

wherein $R_1$ represents an optionally substituted aryl radical, $R_2$ represents hydrogen, lower alkyl, lower alkenyl, acyl or α-aryl-lower alkyl, $R_3$ represents a free or substituted hydroxyl group, alk represents a lower alkylene radical which separates the two nitrogen atoms by 2 or 3 carbon atoms, $R_4$ represents hydrogen or lower alkyl and n represents 1 to 4, and their salts, as well as processes for their manufacture and pharmaceutical compositions comprising such compounds as well as a process for lowering the blood pressure (for treating hypertension) and/or treating tachycardia characterised in that such compositions are administered to a mammal.

An optionally substituted aryl radical $R_1$ is, for example, a monosubstituted, disubstituted or polysubstituted phenyl or naphthyl radical or an unsubstituted phenyl or naphthyl radical and also, for example, an optionally substituted 5,6,7,8-tetrahydro-1-naphthyl radical or 2-naphthyl radical. A monosubstituted or disubstituted phenyl or naphthyl radical and especially a monosubstituted phenyl radical or naphthyl radical and very particularly a monosubstituted phenyl radical, are preferred.

The aryl radical $R_1$ is substituted, for example, by aliphatic hydrocarbon radicals, especially by lower aliphatic hydrocarbon radicals which can also be substituted. Examples of such optionally substituted lower aliphatic hydrocarbon radicals are lower alkyl groups, lower alkenyl groups, lower alkynyl groups, lower alkoxy-lower alkyl groups, lower alkylthio-lower alkyl groups, hydroxy-lower alkyl groups, halogen-lower alkyl groups, lower alkoxycarbonylamino-lower alkyl groups and acylamino-ethenyl groups.

A substituent of an aryl radical $R_1$ can also be hydroxyl which is optionally etherified by an aliphatic hydrocarbon radical, especially by a lower aliphatic hydrocarbon radical, which can be substituted yet further. Examples of such radicals are lower alkoxy groups, lower alkenyloxy groups, lower alkynyloxy groups, lower alkoxy-lower alkoxy groups, lower alkylthio-lower alkoxy groups, aryl-lower alkoxy groups, such as phenyl-lower alkoxy groups, for example benzyloxy groups, and hydroxyl groups.

The aryl radical $R_1$ can also be optionally substituted by the following substituents: Alkanoyl groups, alkanoyloxy groups, lower alkylthio groups, acylamino groups, hydrogen atoms or cyano, amino and/or nitro groups.

Further substituents of the aryl radical $R_1$ are optionally substituted carbamoyl groups, such as, for example, N-lower alkylcarbamoyl groups, N,N-di-lower alkylcarbamoyl groups or N,N-lower alkylenecarbamoyl groups.

An optionally substituted ureido group can also be a substituent of the aryl radical $R_1$.

Particularly suitable substituents of the aryl radical $R_1$ can optionally substituted carbamoyl groups, lower alkoxy-carbonylamino-lower alkyl groups, lower alkoxy-lower alkoxy groups, acylamino-ethenyl groups, lower alkylthio-lower alkoxy groups, the hydroxyl group and alkanoyl groups, nitrile groups and especially acylamino groups and very particularly lower alkoxy groups, lower alkenyl groups, lower alkenyloxy groups and halogen atoms.

Lower radicals in the preceding and following text are above all radicals which contain up to 7 C atoms, in particular up to 4 C atoms.

Lower alkyl radicals are, for example, methyl, ethyl, n-propyl or isopropyl, or straight-chain or branched butyl, pentyl or hexyl, which can be bonded in any desired position.

Lower alkoxy radicals are, in particular, radicals which preferably have up to 7 C atoms in the lower alkyl part, especially up to 4 C atoms, with lower alkyl having the above meaning. Examples of such lower alkoxy radicals are methoxy, ethoxy, n-propoxy, isopropoxy, n-butoxy and n-amyloxy. Two lower alkoxy radicals, especially two adjacent lower alkoxy radicals, can also be linked, as lower alkylenedioxy, for example methylenedioxy.

Examples of lower alkenyl radicals are vinyl, propenyl, allyl or methallyl. Examples of lower alkenyloxy radicals are allyloxy, metallyloxy or propenyloxy.

Examples of lower alkoxy-lower alkyl radicals are those which have up to 7 C atoms, preferably up to 4 C atoms, in each lower alkyl part, for example methoxymethyl, ethoxymethyl, n-propoxymethyl, n-butoxymethyl, 2-(n-butoxy)-ethyl, 3-(n-propoxy)-propyl or particularly 2-methoxyethyl.

Examples of lower alkoxy-lower alkoxy radicals are those which contain up to 7 C atoms, preferably up to 4 C atoms, in each lower alkyl part, with the lower alkyl part having the above meaning. Examples of such radicals are, for instance, methoxy-methoxy, ethoxymethoxy, 1-methoxyethoxy, 4-methoxy-n-butoxy, 3-methoxy-n-butoxy and especially 3-methoxy-n-propoxy, 2-methoxyethoxy and 2-ethoxyethoxy.

Lower alkinyl radicals are in particular propargyl radicals: lower alkinyloxy radicals are, in particular, propargyloxy radicals.

As alkanoyl radicals there should above all the mentioned lower alkanoyl radicals, such as propionyl or butyryl radicals, but above all the acetyl radical; examples of alkanoyloxy radicals are those in which the alkanoyl part has the above meaning.

Examples of lower alkylmercapto groups are groups in which the lower alkyl part is defined as above. Examples of such groups are ethylmercapto, isopropylmercapto, n-butylmercapto and especially methylmercapto.

Lower alkylthio-lower alkyl groups have, for example, up to 7 C atoms, preferably up to 4 C atoms, in each lower alkyl part and are thus, for example, methylthiomethyl, 2-ethylthioethyl, 3-methylthio-n-propyl and especially 2-methylthioethyl.

Lower alkylthio-lower alkoxy groups are, for example, groups which possess up to 7 C atoms, preferably up to 4 C atoms, in each lower alkyl part. Examples of such groups are methylthiomethoxy, 2-ethylthioethoxy, 3-methylthio-n-propoxy and especially 2-methylthioethoxy.

Hydroxy-lower alkyl groups are above all those with at most 7 C atoms, preferably with at most 4 C atoms, in which the lower alkyl part has the above meaning, such as, for example, 2-hydroxyethyl, 3-hydroxy-n-propyl and especially hydroxymethyl.

Possible halogen atoms are in particular fluorine atoms, or bromine atoms and especially chlorine; examples of halogenolower alkyl groups are in which the lower alkyl part has the above meaning, for example chloromethyl, 2-chloroethyl, dichloromethyl and especially trifluoromethyl.

N-Lower alkylcarbamoyl groups contain, as the lower alkyl part, in particular the radicals singled out above. N,N-Di-lower alkylcarbamoyl groups for example contain the radicals described above as the lower alkyl part. N,N-Lower alkylenecarbamoyl in particular contains, as the lower alkylene part, butylene-1,4 or pentylene-1,5. Examples of such radicals are N-methylcarbamoyl, N,N-dimethylcarbamoyl, pyrrolidino-carbonyl and piperidino-carbonyl.

An optionally substituted ureido group is a group in which the free amino group can optionally be substituted by lower alkyl groups, with lower alkyl having the above meaning, such as, for example, a N', N'-dimethylureido group or N',N'-diethylureido group. If the ureido group is substituted by divalent radicals, these radicals, which can optionally be interrupted and/or substituted by hetero-atoms, are preferably lower alkylene radicals which can be straight-chain or branched and above all possess 4-6 chain carbon atoms if the carbon chain is uninterrupted or 4 or 5 carbon atoms if the carbon chain is interrupted by hetero-atoms. Possible hetero-atoms are, in particular, oxygen, sulphur and nitrogen. Examples of such radicals are butylene-(1,4), pentylene-(1,5), hexylene-(1,5), hexylene-(2,5), hexylene-(1,6), heptylene-(1,6), 3-oxapentylene-(1,5), 3-oxahexylene-(1,6), 3-thia-pentylene-(1,5), 2,4-dimethyl-3-thia-pentylene-(1,5), 3-aza-pentylene-(1,5) and 3-lower alkyl 3-aza-pentylene-(1,5), such as 3-methyl-3-azapentylene-(1,5) or 3-aza-hexylene-(1,6). N'-Lower alkylureido, such as N'-methylureido, and the above N', N'-di-lower alkylureido are also suitable as ureido.

By lower alkoxycarbonylamino-lower alkyl groups there are understood radicals of which the lower alkyl part possesses, for example, up to 7 C atoms, preferably up to 4 C atoms, both in the lower alkoxy part and in the lower alkyl part itself. Examples of such groups are methoxycarbonylaminomethyl, ethoxycarbonylaminomethyl, 4-methoxycarbonylamino-n-butyl, 2-ethoxycarbonylaminoethyl, 3-ethoxycarbonylamino-n-propyl and particularly 2-methoxycarbonylaminoethyl and 3-methoxycarbonylamino-n-propyl.

Acylamino groups are especially those which contain cycloaliphatic, aromatic, araliphatic and above all aliphatic acyl radicals as acyl radicals.

Aliphatic acyl radicals of the formula R-CO- are especially those in which R is a lower alkyl radical. Examples of lower alkyl radicals are those with at most 7 C atoms, such as the methyl, ethyl, iso- and n-propyl radical and straight and branched butyl, pentyl and hexyl radicals bonded in any desired position.

Cycloaliphatic acyl radicals of the formula R'-CO- are especially those in which R' denotes an optionally loweralkylated lower cycloalkyl radical, above all with 3-7, in particular 5-7, ring members, such as, for example, the cyclopropyl, cyclopentyl, cyclohexyl and cycloheptyl radical.

Benzoyl and naphthoyl radicals, or phenyl-lower alkanoyl radicals, such as phenylacetyl or α- and β-phenylpropionyl radicals, may be mentioned as examples of aromatic or araliphatic acyl radicals, respectively.

The acyl radicals mentioned can be substituted yet further.

The following may be mentioned as examples of substituents of the aromatic and araliphatic acyl radicals, with the substituents preferably being located on the rings: Lower alkyl radicals, such as those mentioned above, halogen atoms, such as fluorine, bromine and iodine and especially chlorine, the pseudo-halogen trifluoromethyl, and lower alkoxy groups. One, two or more such substituents can be present.

Preferred acyl radicals are benzoyl and especially acetyl.

Acylamino-ethylene groups are in particular radicals of the formula

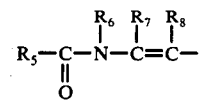

wherein $R_5$ is a lower alkyl group having the above meaning, a lower alkoxy group having the above meaning or an amino group, that is to say a primary, secondary or tertiary amino group, preferably lower alkylamino or di-lower alkylamino, with the lower alkyl part in each case having the above meaning; $R_6$ is hydrogen or a lower alkyl group having the above meaning; $R_7$ is hydrogen, a lower alkyl group having the above meaning, carboxyl or lower alkoxycarbonyl, in which the lower alkoxy part has the above meaning; $R_8$ is hydrogen or a lower alkyl group having the above meaning.

Lower alkyl or lower alkenyl groups $R_2$ are in particular the lower alkyl or lower alkenyl groups indicated above and defined in more detail as substituents of the aryl radical $R_1$. Examples of acyl radicals $R_2$ are radicals of which the acyl part in particular has the meaning indicated above for acylamino groups, above all a lower alkanoyl radical, such as an acetyl group or aroyl, for example optionally substituted benzoyl, suitable substituents being, for example, lower alkyl, lower alkoxy, halogen and/or trifluoromethyl, and the benzoyl radical in particular requiring to be singled out.

An α-aryl-lower alkyl radical is, for example, an optionally substituted phenylalkyl or naphthylalkyl radical or an optionally substituted 5,6,7,8-tetrahydro-1- or 2-naphthylalkyl radical. An optionally substituted phenyllower alkyl radical, and very particularly the benzyl radical, is preferred. Suitable substituents of the aryl part of the α-aryl-lower radical are above all lower alkyl radicals, halogen atoms or the substituents indicated under the definition of $R_1$ being aryl.

A substituted hydroxyl group $R_3$ is, for example, an etherified hydroxyl group or, preferably, an esterified hydroxyl group.

By an etherified hydroxyl group there is above all understood a hydroxyl group etherified by a lower alkyl group, in which the lower alkyl part has the above meaning. Examples of such radicals are n-propoxy, ethoxy and especially methoxy groups.

An esterified hydroxyl group is, for example, an acyloxy group of which the acyl part in particular has the meaning indicated above for acylamino groups. Particular interest attaches to hydroxyl groups esterified by aliphatic acyl radicals of the formula R-CO-, in which R in particular is a lower alkyl radical, that is to say lower alkanoyloxy radicals. Examples of such radicals are propionyloxy, butyryloxy and especially acetoxy.

Lower alkyl groups $R_4$ are, in particular, the above mentioned radicals, for example ethyl, n-propyl, isopropyl and especially methyl.

A lower alkylene radical alk is, in particular, a straight or branched lower alkylene radical which possesses 2 or 3 chain carbon atoms but can in total contain up to, for example 7, especially 4, C atoms. Preferably, alk is an optionally lower-alkylated dimethylene or trimethylene radical, especially a dimethylene or trimethylene radical which is optionally monosubstituted by lower akyl which has the above meaning, and very particularly an unsubstituted dimethylene or trimethylene radical, The new compounds possess valuable pharmacological properties. Thus they show a blood pressure-lowering action, as can be shown in animal experiments, for example on intravenous administration of doses of about 1-100 mg/kg to narcotised cats. In addition, the new compounds produce an antitachycardia and α-sympathicolysis as can again be shown in animal experiments, for example in experiments carried out in vitro at concentrations of 3-100 γ/ml on guinea-pigs (Langendorff preparation) or in vitro experiments at concentrations of 0.1 to 100 γ/ml on rats (isolated perfused mesenterial artery). The new compounds are therefore useful as anti-hypertensive agents, antitachycardia agents and α-sympathicolytic agents. The new piperidines can furthermore serve as starting products or intermediate products for the manufacture of other, especially of therapeutically active, compounds.

Compounds to be particularly mentioned are compounds of the formula I, wherein $R_1$ is a phenyl radical which is optionally substituted in the p-, m- and/or preferably o-position, $R_2$ is hydrogen, lower alkyl, lower alkenyl, acyl or benzyl, $R_3$ is a free, etherified or esterified hydroxy group, $R_4$ is hydrogen or lower alkyl and $n$ is 1-4 and alk is an optionally loweralkylated-dimethylene or trimethylene radical.

Further compounds to be singled out are compounds of the formula I, wherein $R_1$ is a phenyl radical which is monosubstituted or disubstituted by lower alkyl, lower alkoxy, lower alkenyl, lower alkenyloxy, halogen, halogeno-lower alkyl, carbamoyl which is optionally substituted by lower alkyl groups, lower alkoxycarbonylamino-lower alkyl, lower alkoxy-lower alkoxy, acylamino-ethenyl, lower alkylthio-lower alkoxy, hydroxyl, lower alkanoyl, lower alkoxyalkyl, lower alkinyl, lower alkylthio-lower alkyl, hydroxy-lower alkyl, lower alkanoyloxy, lower alkylthio, acylamino, nitrile, amino, nitro, optionally substituted ureido and/or lower alkinyloxy, $R_2$ is hydrogen, lower alkyl, lower alkenyl or lower alkanoyl, $R_3$ is a free hydroxyl group, a lower alkanoyloxy group or a lower alkoxy group and $R_4$ is hydrogen or lower alkyl, with $n$ being 1 and alk being an optionally mono-lower alkylated dimethylene or trimethylene radical. Furthermore, $R_1$ can also be unsubstituted phenyl or naphthyl and the other substituents can have the meanings indicated for the group of compounds Id.

Compounds to be singled out very particularly are compounds Id of the formula I, wherein $R_1$ is phenyl which is monosubstituted by lower alkyl, lower alkoxy, lower alkenyl, lower alkenyloxy, halogen, optionally lower alkyl-substituted carbamoyl, lower alkoxycarbonylamino-lower alkyl, lower alkoxy-lower alkoxy, lower alkanoylaminoethenyl, lower alkylthio-lower alkoxy, hydroxyl or lower alkanoyl, $R_2$ is hydrogen, lower alkyl, lower alkenyl or lower alkanoyl, $R_3$ is free hydroxyl or lower alkanoyloxy, $R_4$ is hydrogen or lower alkyl, with $n=1$, and alk is an optionally monolower alkylated ethylene or trimethylene radical.

Compounds to be mentioned very particularly are compounds of the formula I, wherein $R_1$ is a phenyl radical which is monosubstituted by lower alkyl, lower alkoxy, lower alkenyl, lower alkenyloxy, lower alkanoyl, lower alkanoylamino, hydroxyl, N-lower alkyl-carbamoyl or halogen, $R_2$ is hydrogen or lower alkyl, $R_3$ is hydroxyl, $R_4$ is hydrogen and alk is an optionally monomethylated ethylene or trimethylene radical.

Compounds to be singled out very particularly are piperidines of the formula I, wherein R is phenyl monosubstituted by methyl, methoxy, allyl, allyloxy, hydroxyl, acetylamino, propionyl, N-methyl-carbamoyl or chlorine, $R_2$ is hydrogen or methyl, $R_3$ is hydroxyl, $R_4$ is hydrogen and alk is ethylene or trimethylene.

Especially valuable are the compounds of the formula

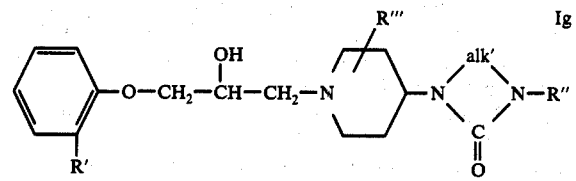

in which R' stands for halogen, lower alkyl or lower alkoxy, especially for chlorine or paticularly for methyl or methoxy, R" for lower alkyl, such as ethyl or especially methyl, or particularly hydrogen, R'" for methyl or especially hydrogen and alk' for ethylene or trimethylene and above all 1-[3-(o-chlorophenoxy)-2-hydroxypropyl]-4-(2-oxo-1-imidazolidinyl)-piperidine, 1-[3-(o-methoxyphenoxy)-2-hydroxypropyl]-4-(3-methyl-2-oxo-1-imidazolidinyl)-piperidine, 1-[3-(o-chlorophenoxy)-2-hydroxypropyl]-4-(2-oxo-hexahydro-1-pyrimidinyl)-piperidine or particularly 1-[3-(o-methylphenoxy)-2-hydroxypropyl]-4-(2-oxo-hexahydro-1-pyrimidinyl)-piperidine, 1-[3-(o-methoxyphenoxy)-2-hydroxypropyl]-4-(2-oxo-hexahydro-1-pyrimidinyl)-piperidine, 1[3-(o-methylphenoxy)-2-hydroxypropyl]-4-(2-oxo-1-imidazolidinyl)-piperidine and especially 1[3-(o-methoxyphenoxy)-2-hydroxypropyl]-4-(2-oxo-1-imidazolidinyl)-piperidine, which in renal hypertonic dogs in a dose of 50 mg/kg p.o. shows a significant antihypertensive action, coupled with good toleration.

The new compounds are obtained according to methods which are in themselves known.

For example, it is possible to react a compound of the formula IIa

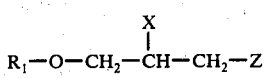

(IIa)

with a compound of the formula IIIa

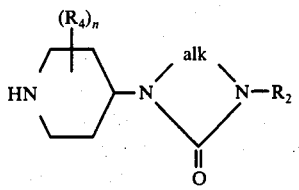

(IIIa)

wherein $R_1$, $R_2$, $R_4$, $n$ and alk have the above meaning and either X represents a free or substituted hydroxyl group $R_3$, and Z represents a reactive esterified hydroxyl group or X and Z together form an epoxy group.

A reactive, esterified hydroxyl group is in particular a hydroxyl group esterified by a strong inorganic or organic acid, above all a hydrohalic acid, such as hydrochloric acid, hydrobromic acid or hydriodic acid, or an organic sulfonic acid, such as an aromatic sulfonic acid, for example benzenesulphonic acid, p-bromobenzenesulphonic acid or p-toluensulphonic acid. Thus Z in particular represents chlorine, bromine or iodine.

The reaction is carried out in the usual manner. If a reactive ester is used as the starting material, the reaction is preferably carried out in the presence of a basic condensation agent and/or with an excess of the compound of the formula IIIa.

In resulting compounds, substituents can be split off, introduced or modified within the framework of the end products.

Thus it is possible, in a resulting compound of the formula I, wherein $R_1$ is an aryl radical substituted by a functionally modified carboxyl group and the other substituents have the above meaning, to convert this radical into an aryl radical substituted by a carbamoly group, N-lower alkylcarbamoyl group, N,N-di-lower alkylcarbamoyl group or N,N-lower alkylenecarbamoyl group, for example by reaction with an optionally N-mono- or N-di-alkyl substituted amine or N,N-lower alkylene-substituted amine.

An optionally functionally modified carboxyl group is above all a carboxyl group esterified with an alcohol or phenol. Examples of suitable alcohols are lower alkanols, such as ethanol of methanol. Examples of suitable phenols are phenol or p-nitrophenol.

The reaction is carried out in the usual manner, especially at an elevated temperature, and if appropriate at a drastically elevated temperature, such as up to more than 200° C, under pressure if desired, and with an excess of the particular amine if desired, If the reaction is carried out at room temperature or only moderately elevated temperature, it is preferably carried out in an inert solvent, allowing a longer reaction time. Examples of inert solvents are alcohols, such as methanol or ethanol, ethers, such as diethyl ether or dioxane, benzene and the like.

Furthermore it is possible, in resulting compounds of the formula I, wherein $R_2$, $R_3$, $R_4$, $n$ and alk have the above meaning and $R_1$ is an aryl radical substituted by a hydroxyl group, to convert this radical $R_1$ either into an aryl radical substituted by lower alkoxy-lower alkoxy, for example by reaction with a compound of the formula lower alkoxy-lower alkyl-$Z_1$, wherein $Z_1$ is a reactive esterified hydroxyl group, or to convert $R_1$ into an aryl radical substituted by a lower alkoxy group, for example by reaction with a compound of the formula lower alkyl-$Z_1$, wherein $Z_1$ is a reactive esterified hydroxyl group, or to convert $R_1$ into an aryl radical substituted by a lower alkenyloxy group, such as, for example, by reaction with a compound of the formula alkenyl-$Z_1$, wherein $Z_1$ is a reactive esterified hydroxyl group. The reactants can in particular be used in the form of their salts.

In resulting compounds in which $R_2$ is hydrogen, the latter can be replaced in the usual manner by a lower alkyl or lower alkenyl radical, especially in accordance with the processes described above, by reacting a compound of the formula I, wherein $R_1$, $R_3$, $R_4$, $n$ and alk have the above meaning and $R_2$ is hydrogen, with a compound of the formula lower alkyl-(lower alkenyl)-Z, wherein Z is a reactive esterified hydroxyl group.

The reactions mentioned can optionally be carried out simultaneously or successively and in optional sequence.

The reactions mentioned are carried out in the usual manner in the presence or absence of diluents, condensation agents and/or catalytic agents, at lowered, ordinary or elevated temperature, and in a closed vessel if desired.

Depending on the process conditions and starting substances, and end products are obtained in the free form or in the form of their acid addition salts which is also included in the invention. Thus, for example, basic, neutral or mixed salts and optionally also hemihydrates, monohydrates, sesquihydrates or polyhydrates thereof, can be obtained. The acid addition salts of the new compounds can be converted into the free compound in a manner which is in itself known, for example with basic agents, such as alkalis or ion exchangers. On the other hand, the free bases obtained can form salts with organic or inorganic acids. To manufacture acid addition salts, those acids are in particular used which are suitable for forming therapeutically usable salts. As examples of such acids there may be mentioned: Hydrogen halide acids, for example hydrochloric acid, sulphuric acids, for example sulphuric acid, phosphoric acids, nitric acid, perchloric acid, aliphatic, alicyclic, aromatic or heterocyclic carboxylic acids or sulphonic acids, such as formic acid, acetic acid, propionic acid, succinic acid, glycollic acid, lactic acid, malic acid, tartaric acid, citric acid, ascorbic acid, maleic acid, hydroxymaleic acid or pyruvic acid, fumaric acid, benzoic acid, p-aminobenzoic acid, anthranilic acid, p-hydroxybenzoic acid, salicylic acid or p-aminosalicylic acid, embonic acid, methanesulphonic acid, ethanesulphonic acid, hydroxyethanesulphonic acid, ethylenesulphonic acid, halogenobenzenesulphonic acids, toluenesulphonic acid, naphthalenesulphonic acid or sulphanilic acid, methionine, tryptophane, lysine or arginine.

These or other salts of the new compounds, such as, for example, the picrates, can also be used for purifying the resulting free bases, by converting the free bases into salts, isolating these and again liberating the bases from the salts. Because of the close relationships between the new compounds in the free form and in the form of their salts, the free compounds are to be understood, in the proceding and following text, where appropriate also to include the corresponding salts, with regard to general sense and intended use.

The invention also relates to those embodiments of the process according to which a compound obtainable as in intermediate product at any stage of the process is used as the starting compound and the missing process steps are carried out, or the process is stopped at any stage, or in which a starting substance is formed under the reaction conditions or in which a reactant is present in the form of its salts, if appropriate.

The new compounds can, depending on the choice of the starting substances and procedures, be in the form of optical antipodes or racemates or, if they contain at least two asymmetrical carbon atoms, also racemate mixtures and/or pure geometrical isomers or mixtures thereof (isomer mixtures).

Isomer mixtures obtained can be separated, on the basis of the physico-chemical differences of the constituents, in a known manner into the two pure geometrical isomers, for example by chromatography on a suitable stationary phase, such as silica gel or aluminium oxide which have been pretreated with a complex-forming heavy metal compound, for example with a silver compound, or by forming a heavy metal addition compound, for example the silver nitrate complex, separating the latter into the addition compounds of the pure isomers, for example by fractional crystallisation, and subsequently liberating the pure isomers.

Resulting pure isomers, for example trans-isomers, can be converted in the usual manner, for example photochemically, for example by irradiation with light of a suitable wavelength, advantageously in a suitable solvent, such as an aliphatic hydrocarbon, or in the presence of a suitable catalyst, into the particular isomers of opposite configuration, for example into the cis-isomers.

Racemate mixtures can be separated in a known manner, on the basis of the physico-chemical differences of the constituents, into the two stereoisomeric (diastereomeric) pure racemates, for example by chromatography and/or fractional crystallisation.

Resulting racemates can be resolved according to known methods, for example by recrystallisation from an optically active solvent, with the aid of micro-organisms or by reaction with an optically active acid which forms salts with the racemic compound and separation of the salts obtained in this manner, for example on the basis of their different solubilities, into the diastereomers, from which the antipodes can be liberated by the action of suitable agents. Particularly customary optically active acids are, for example, the D- and L-forms of tartaric acid, di-o-toluyltartaric acid, malic acid, mandelic acid, camphorsulphonic acid or quinic acid. Advantageously, the more active L-antipode is isolated.

Appropriately, those starting substances are used for carrying out the reactions according to the invention which lead to the initially particularly mentioned groups of end products and especially to the end products which have been particularly described or singled out.

A compound of the formula IIIa can be manufactured by hydrogenating compounds of the formula VI

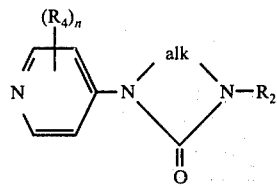

preferably catalytically as described above.

Compounds of the formula IIIa are new and are used as intermediate products for the manufacture of compounds of the formula I and also from a subject of the invention.

The starting compounds are known or can, if they are new, be obtained according to methods which are in themselves known.

The new compounds can be used as medicines, for example in the form of pharmaceutical compositions, in which they are present in their free form or in the form of their therapeutically acceptable salts, in admixture or conjunction with a pharmaceutical, organic or inorganic, solid or liquid excipient which is suitable, for example, for enteral, e.g. oral, or parenteral administration. Possible substances for forming the excipient are those which do not react with the new compounds, such as, for example, water, gelatine, lactose, starch, magnesium stearate, talc vegetable oils, benzyl alcohols, gum, polyalkylene glycols, white petroleum jelly, cholesterol or other known medicinal excipients. The pharmaceutical preparation can, for example, be in the form of tablets, dargees, capsules, suppositories, ointments or creams or in aliquid form as solutions (for example as an elixir or syrup), suspensions or emulsions. They are optionally sterilised and/or contain auxiliaries, such as preservatives, stabilisers, wetting agents or emulsifiers, or salts for regulating the osmotic pressure or buffers. They can also contain yet other therapeutically valuable substances. The compositions, which can also be employed in veterinary medicine, are obtained according to customary methods.

The dosage of the compositions, of the invention depends on the nature of the conditions to be treated and the individual requirements. For example, the new compounds mentioned above can be administered orally to a mammal of approximately 75 kg bodyweight in daily dosages of about from 30 to 300 mg.

The invention also concerns a process for treating tachycardia and/or hypertension wherein a composition referrd to above or below is administered to mammal.

The new compounds can also be used advantageously in pharmaceutical compositions in combination with other anti-hypertensive agents and/or diuretics.

Possible anti-hypertensive compounds are in particular those of the type of α-amino-β-hydroxyphenyl-pripionic acid, β-amino-β-alkoxyphenyl-propionic acid and especially the hydrazinopyridazines and the sympathicolytic agents.

Suitable α-amino-β-hydroxyphenyl-propionic acids are especially those which are lower-alkylated, above all methylated, in the α-position, such as, above all, α-amino-α-methyl-β-(3,4-dihydroxyphenyl)-propionic acid, optionally in the form of its antipode which is laevo-rotatory in aqueous hydrochloric acid.

Suitable β-amino-β-alkoxyphenyl-propionic acids are especially those which contain lower alkoxy radicals, preferably with up to 6, especially with up to 3, C atoms, and especially methoxy groups, in the alkoxyphenyl part, such as, above all, β-amino-β-(3,4-dimethoxyphenyl)-propionic acid, optionally in the form of its dextro-rotatory antipode.

A suitable hydrazinopyridazine is in particular a hydrazinophthalazine, such as 1,4-dihydrazinophthalazine, preferably in the form of one of its salts, such as of the sulphate, as well as 1-hydrazinophthalazine.

Suitable sympathicolytic agents are especially imidazole derivatives, such as 2-benzyl-4,5-imidazoline, preferably in the form of one of its salts, such as the hydrochloride, and 2-[(N-p-tolyl)-N-(m-hydroxyphenyl)-aminomethyl]-imidazoline, preferably in the form of one of its salts, such as the hydrochloride or methanesulphonate.

Suitable sympathicolytic agents are above all antihypertonic agents which act on the peripheral part of the sympathetic nervous system, such as sympathetic inhibitors, for example N-o-bromobenzyl-N-ethyl-N,N-dimethylammonium p-toluenesulphonate and especially guanidine derivatives, such as 1,2,3,4-tetrahydroisoquinoline-2-carboxamidine, preferably in the form of one of its salts, such as the sulphate, 7-bromo-1,2,3,4-tetrahydroisoquinoline-2-carboxamidine, preferably in the form of one of its salts, such as the sulphate, 1-benzyl-2,3-dimethylguanidine, preferably in the form of one of its salts, such as the sulphate, and above all β-(1-azacyclooctyl)ethylguanidine, preferably in the form of one of its salts, such as the sulphate.

Suitable diuretics are substances which increase diuresis both through renal and through extra-renal action on the tissues. For this purpose it is possible to use substances having an inhibiting action on the reverse-resorption in the tubulus, such as, for example, in particular saluretics and ethacrinic acid and its analogues.

Particularly suitable substances are benzothiadiazine derivatives, such as thiazides and hydrothiazides, benzenesulphonamides, phenoxyacetic acids, benzofurane-2-carboxylic acids and benzofurane-2,3-dihydro-2-carboxylic acids.

Particularly suitable thiazides are those of the formula XII

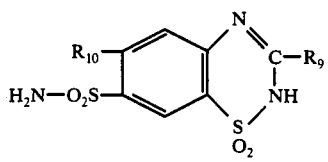

(XII)

wherein $R_9$ is a hydrogen atom or a phenyl-lower alkylthiolower alkyl and $R_{10}$ is a halogen atom or the trifluoromethyl group.

A phenyl-lower alkylthio-lower alkyl radical $R_9$ is especially a radical wherein the lower alkyl parts have up to 4 C atoms and especially 1 C atom and wherein the phenyl part is unsubstituted, such as the benzyl-thiomethyl radical.

A halogen atom $R_{10}$ is a bromine atom, iodine atom or fluorine atom or especially a chlorine atom.

Amongst these compounds of the formula XII there should above all be mentioned 6-chloro-7-sulphamyl-1,2,4-benzothiadiazine-1,1-dioxide, 6-trifluoromethyl-7-sulphamyl-1,2,4-benzothiadiazine-1,1-dioxide and 2-benzylthiomethyl-6-chloro-7-sulphamyl-1,2,4-benzothiadiazine-1,1-dioxide.

Particularly suitable hydrothiazides are those of the formula XIII

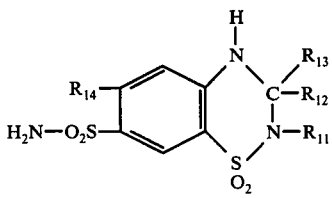

(XIII)

wherein $R_{11}$ is hydrogen or lower alkyl, $R_{12}$ is hydrogen, lower alkyl, lower alkenyl, cycloalkyl, cycloalkenyl, cycloalkyllower alkyl, aryl, aryl-lower alkyl, halogeno-lower alkyl, lower alkylthio-lower alkyl, lower alkenylthio-lower alkyl, halogeno-lower alkylthio-lower alkyl, phenyl-lower alkylthio-lower alkyl or heterocycloalkyl-lower alkyl, $R_{13}$ is hydrogen or together with $R_{12}$ represents lower alkylene and $R_{14}$ is halogen or trifluoromethyl.

A lower alkyl radical $R_{11}$ is especially a radical with up to 7 C atoms, above all with up to 4 C atoms, such as ethyl, n-propyl, i-propyl, straight or branched butyl, pentyl, hexyl or heptyl bonded in any desired position, and above all methyl.

A lower alkyl radical $R_{12}$ is especially a radical as indicated for $R_{11}$ and above all methyl, ethyl or isobutyl.

A lower alkenyl radical $R_{12}$ is especially a radical with up to 7, especially up to 4, C atoms, such as allyl.

A cycloalkyl radical $R_{12}$ is especially a radical with 3-8, above all 5-7, ring C atoms and a total of preferably up to 8, especially up to 7, C atoms, such as cyclopentyl and cyclohexyl.

A cycloalkenyl radical $R_{12}$ is especially a radical with 5-8, above all 5-7, ring C atoms and a total of preferably up to 8 and especially up to 7 C atoms, such as cyclopentenyl, cyclohexenyl or norbornenyl, especially 5-norbornen-2-yl.

A cycloalkyl-lower alkyl radical $R_{12}$ is especially a radical wherein the cycloalkyl part and the lower alkyl part have the above meaning, above all cyclopentylmethyl.

An aryl radical $R_{12}$ is especially a radical with 6 carbon atoms, such as phenyl, which can be substituted by lower alkyl, such as methyl, lower alkoxy, such as methoxy, halogen, such as chlorine, or trifluoromethyl.

An aryl-lower alkyl radical $R_{12}$ is especially a radical wherein the lower alkyl part has the above meaning and the aryl part is phenyl substituted by lower alkyl, such as methyl, lower alkoxy, such as methoxy, halogen, such as chlorine, or trifluoromethyl, or is in particular unsubstituted phenyl, such as benzyl or 1-phenylethyl.

A halogeno-lower alkyl radical $R_{12}$ is especially a lower alkyl radical carrying one, two or three halogen atoms, wherein the lower alkyl part in particular has the above meaning, such as, in particular, halogenomethyl, for example trifluoromethyl, chloromethyl, dichloromethyl and trichloromethyl.

A lower alkylthio-lower alkyl radical $R_{12}$ is especially a radical wherein the lower alkyl part and the lower alkyl part of the lower alkylthio part have the meanings given for lower alkyl above, such as methylthiomethyl and 2-methylthioethyl.

A lower alkenylthio-lower alkyl radical $R_{12}$ contains, for example, one of the abovementioned lower alkenyl radicals and is, for example, allylthiomethyl.

A halogeno-lower alkylthio-lower alkyl radical $R_{12}$ is in particular a radical as indicated for the lower alkylthio-lower alkyl radical $R_{12}$ which carries one, two or three halogen atoms, such as 2,2,2-trifluoroethylthiomethyl.

A phenyl-lower alkylthio-lower alkyl radical $R_{12}$ is in particular a radical wherein the lower alkyl parts have the above meaning, such as benzylthiomethyl.

A heterocycloalkyl-lower alkyl radical is, for example, a radical with one or more hetero-atoms in a 3-membered to 10-membered ring, especially a 5-membered ring, such as, for example, a furyl radical or a pyrrolyl radical, and with a lower alkyl part which has up to 7 C atoms, above all up to 4 C atoms, such as ethyl, n-propyl, straight or branched butyl, pentyl, hexyl or heptyl bonded in any desired position, and above all methyl.

A lower alkylene radical formed by $R_{12}$ and $R_{13}$ together is especially a lower alkylene radical with up to 7, above all with up to 6, C atoms, and especially with at least 2, and in particular with at least 4, C atoms in the alkylene chain, such as 1,5-pentylene and 3-methyl-1,5-pentylene.

A halogen atom $R_{14}$ is bromine, iodine or fluorine and especially chlorine.

Amongst these compounds of the formula XIII there should above all be mentioned: 3-Ethyl-6-chloro-7-sulphamyl-3,4-dihydro-1,2,4-benzothiadiazine-1,1-dioxide; 3-trichloromethyl-6-chloro-7-sulphamyl-3,4-dihydro-1,2,4-benzothiadiazine-1,1-dioxide; 3-benzyl-6-trifluoromethyl-7-sulphamyl-3,4-dihydro-1,2,4-benzothiadiazine-1,1-dioxide; 2-methyl-3-(2,2,2-trifluoroethylthiomethyl)-6-chloro-7-sulphamyl-3,4-dihydro-1,2,4-benzothiadiazine-1,1-dioxide; 3-(2,2,2-trifluoroethylthiomethyl)-6-chloro-7-sulphamyl-3,4-dihydro-1,2,4-benzothiadiazine-1,1-dioxide; 3-(5-norbornen-2-yl)-6-chloro-7-sulphamyl-3,4-dihydro-1,2,4-benzothiadiazine-1,1-dioxide; 2-methyl-3-chloromethyl-6-chloro-7-sulphamyl-3,4-dihydro-1,2,4-benzothiadiazine-1,1-dioxide; 6-chloro-7-sulphamyl-3,4-dihydro-1,2,4-benzothiadiazine-1,1-dioxide; 3-dichloromethyl-6-chloro-7-sulphamyl-3,4-dihydro-1,2,4-benzothiadiazine-1,1-dioxide; 3-cyclopentylmethyl-6-chloro-7-sulphamyl-3,4-dihydro-1,2,4-benzothiadiazine-1,1-dioxide; 6-trifluoromethyl-7-sulphamyl-3,4-dihydro-1,2,4-benzothiadiazine-1,1-dioxide and 3-isobutyl-6-chloro-7-sulphamyl-3,4-dihydro-1,2,4-benzothiadiazine-1,1-dioxide.

Particularly suitable benzenesulphonamides are those of the formula XIV

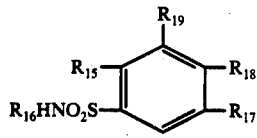

(XVI)

wherein $R_{15}$ is halogen, lower alkyl or trifluoromethyl, $R_{16}$ is hydrogen, lower alkyl, phenyl-lower alkyl, phenyl which is optionally substituted, for example by lower alkoxy or amino, or pyrrolidinomethyl, piperidinomethyl, piperazinomethyl, morpholinomethyl or thiomorpholinomethyl, $R_{17}$ is carboxyl, carbamoyl, N-mono- or N-di-substituted carbamoyl, sulphamoyl, N-mono- or N-di-substituted sulphamoyl, lower alkylsulphonyl or isoindolinyl or is joined to the radical $R_{18}$, $R_{18}$ is hydrogen, lowr alkyl, amino or monosubstituted or disubstituted amino and $R_{19}$ is hydrogen or halogen.

A lower alkyl radical $R_{15}$, $R_{16}$ or $R_{18}$ is in particular one of those mentioned above, above all methyl.

An aminophenyl radical $R_{16}$ is, in particular, a monoaminophenyl radical, such as 4-aminophenyl.

A N-mono-substituted carbamoyl radical $R_{17}$ is in particular a N-lower alkyl-carbamoyl radical, wherein lower alkyl has the above meaning, such as the N-methyl-carbamoyl radical, or a N-amino-substituted carbamoyl radical, wherein the amino group is in particular di-lower alkylamino, such as dimethylamino, or lower alkylideneamino, such as pyrrolidino, piperidino or 2,6-dimethylpiperidino, such as, for example, the N-(2,6-dimethylpiperidino)-carbamoyl radical.

A N-di-substituted carbamoyl radical $R_{17}$ is, in particular, a N-di-lower alkylcarbamoyl radical, wherein lower alkyl has the above meanings, such as the N,N-dimethylcarbamoyl radical.

A N-monosubstituted sulphamoyl radical $R_{17}$ is in particular a N-lower alkyl-sulphamoyl radical, wherein lower alkyl has the above meaning, such as N-methyl-sulphamoyl, a N-furfuryl- or N-tetrahydrofurfuryl-sulphamoyl radical, such as N-furfuryl-sulphamoyl, N-tetrahydrofurfuryl-sulphamoyl, N-(2-methyl-tetrahydrofurfuryl)-sulphamoyl and N-(2-methyl-4-oxotetrahydrofurfuryl)-sulphamoyl.

A N-disubstituted sulphamoyl radical $R_{17}$ is in particular a N,N-di-lower alkylsulphamoyl radical, wherein lower alkyl has the above meaning, such as N,N-dimethyl-sulphamoyl, a N,N-lower alkylene-sulphamoyl radical, wherein lower alkylene in particular has the above meaning, such as piperidino-sulphonyl, a N-lower alkyl-N-carboxy-lower alkyl-sulphamoyl radical, wherein the lower alkyl parts have the above meaning, such as N-methyl-N-carboxy-methyl-sulphamoyl, a N-lower alkyl-N-furfuryl-sulphamoyl radical, wherein lower alkyl has the above meaning, such as N-methyl-N-furfuryl-sulphamoyl, or a N-lower alkyl-N-tetrahydrofurfuryl-sulphamoyl radical, wherein lower alkyl has the above meanings, such as N-methyl-N-(2-methyl-tetrahydrofurfuryl)-sulphamoyl and N-methyl-N-(2-methyl-4-oxotetrahydrofurfuryl)-sulphamoyl.

A lower alkylsulphonyl radical $R_{17}$ is in particular a radical wherein the lower alkyl part has the above meaning, such as methylsulphonyl, ethylsulphonyl and n-butylsulphonyl.

An isoindolinyl radical $R_{17}$ is in particular a 1-isoindolinyl radical having a 3-hydroxy group and a 1-oxo group, such as 3-hydroxy-1-oxo-insoindolinyl-(3).

Radicals $R_{17}$ joined to the radical $R_{18}$ are especially carbamoyl radicals $R_{17}$ which are joined to an amino group $R_{18}$ or a lower alkyl group $R_{18}$, such as 1-oxo-2-cyclohexyl-2-azapropylene-(1,3) and 1-oxo-2,4-bis-aza-3-ethyl-butylene-(1,4).

A monosubstituted amino group $R_{18}$ is in particular a lower alkylamino group, wherein lower alkyl has the above meaning, such as methylamino, or tetrahydrofurfurylamino or especially furfurylamino or benzylamino.

A disubstituted amino group $R_{18}$ is especially a di-lower alkylamino group, wherein lower alkyl has the above meaning, such as dimethylamino, or a di-(phenyl-lower alkyl)-amino group, wherein the lower alkyl part has the above meaning, such as dibenzylamino.

A halogen atom $R_{19}$ is bromine, iodine, fluorine or especially chlorine.

Amongst the compounds of the formula XIV there should especially be singled out those wherein $R_{15}$ is chlorine, $R_{16}$ is aminophenyl, methyl or especially hydrogen, $R_{17}$ is carboxyl, carbamoyl, N-methyl-carbamoyl, N-(2,6-dimethyl-piperidino)-carbamoyl, 3-hydroxyl-1-oxo-isoindolinyl-(3) or N-methyl-N-(2-methyl-tetrahydro-furfuryl)-sulphamoyl or together with $R_{18}$ represents 1-oxo-2-cyclohexyl-2-aza-propylene-(1,3) or 1-oxo-2,4-bis-aza-3-ethyl- butylene-(1,4), $R_{18}$ is hydrogen or furfurylamino and $R_{19}$ is hydrogen.

Amongst these compounds of the formula XIV there should in particular be mentioned 2-chloro-5-N-methylsulphonamido-benzenesulphonamide; 2-chloro-5-N,N-dimethylsulphonamido-benzenesulphonamide; 2-chloro-5-piperidinosulphonyl-benzenesulphonamide;

2-chloro-5-(N-carboxy-methyl-N-methyl)-sulphonamido-benzenesulphonamide; 2-5-(N-furfuryl-sulphonamido)-benzenesulphonamide; 2-chloro-5-(N-tetrahydrofurfuryl-sulphonamido)-benzenesulphonamide; 2-chloro-5-[N-methyl-N-(2-methyl-4-oxo-tetrahydrofurfuryl)-sulphonamido]-benzenesulphonamide; 4,5-dichlorobenzene-1,3-disulphonamide; 4-chloro-6-methylbenzene-1,3-disulphonamide, 4-chloro-6-aminobenzene-1,3-disulphonamide; 2-chloro-5- methylsulphonyl-benzenesulphonamide; 2-chloro-5-ethylsulphonyl-benzenesulphonamide; 2-chloro-5-n-butylsulphonyl-benzenesulphonamide; 2-methyl-5-ethylsulphonyl-benzenesulphonamide; 2-methyl-5-methylsulphonyl-benzenesulphonamide; 2-methyl-5-n-butylsulphonyl-benzenesulphonamide; 2-chloro-4-(N,N-dibenzylamino)-5-carboxyl-benzenesulphonamide; 2-furfurylamino-4-chloro-5-N(p-aminophenyl)-sulphamoyl-benzoic acid, 2-furfurylamino-4-chloro-5-N(o-aminophenyl)-sulphamoyl-benzoic acid and especially 3-sulphonamido-4-chloro-benzoic acid; 3-sulphonamido-4-chloro-benzamide; 3-(N-methylsulphamoyl)-4-chloro-N-methylbenzamide; 1-chloro-4-[N-methyl-N-(2-methyltetrahydrofurfuryl)-sulphamoyl]benzenesulphonamide; 1,3disulphamoyl-4-chlorobenzene; 2-chloro-5-[3-hydroxy-1-oxo-isoindolinyl-(3)]-benzenesulphonamide; 2-ethyl-4-oxo-6-sulphamoyl-7-chloro-1,2,3,4,-tetrahydro-quinazoline; 1-oxo-2-cyclohexyl-5-chloro-6-sulphamoyl-1,2-dihydro-isoindole; 2-chloro-5-[N-(2,6-dimethylpiperidino)-carbamoyl]-benzenesulphonamide; 2-chloro-4-furfurylamino-5-carboxyl-benzenesulphonamide and 2-chloro-4-benzylamino-5-carboxyl-benzenesulphonamide.

Particularly suitable phenoxyacetic acids are those of the formula XV

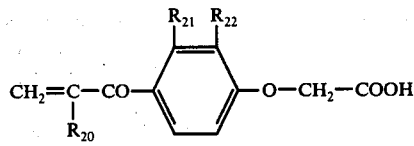

(XV)

wherein $R_{20}$ is lower alkyl, $R_{21}$ is halogen or lower alkyl and $R_{22}$ is hydrogen, halogen or lower alkyl or wherein $R_{21}$ and $R_{22}$ together represent but-1,3-dienylene-(1,4).

A lower alkyl radical $R_{20}$ is, in particular, a radical with 2-7, above 2-4, C atoms, such as one of the above-mentioned radicals, and preferably an unbranched radical of this type, such as n-propyl, n-butyl and especially ethyl.

A halogen atom $R_{21}$ or $R_{22}$ is bromine, iodine or fluorine and especially chlorine.

A lower alkyl radical $R_{21}$ or $R_{22}$ is especially a radical with up to 7, above all up to 4, C atoms, such as, in particular, methyl.

As suitable compounds of the formula XV there should in particular be mentioned [2,3-dimethyl-4-(2-methylene-butyryl)-phenoxy]-acetic acid, [2-methyl-3-chloro-4-(2-methylenebutyryl)-phenoxy]-acetic acid, [4-(2-methylene-butyryl)-1-naphthoxy]-acetic acid and especially [2,3-dichloro-4-(2-methylene-butyryl)-phenoxy]-acetic acid.

Particularly suitable benzofurane-2-carboxylic acids are those of the formula XVI

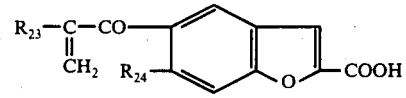

(XVI)

wherein $R_{23}$ is lower alkyl and $R_{24}$ is lower alkyl or lower alkoxy.

A lower alkyl radical $R_{23}$ is especially a radical with 2-7, above all 2-4, C atoms, such as one of those mentioned above, and preferably an unbranched radical of this type, such as ethyl.

A lower alkyl radical $R_{24}$ is especially a radical with up to 7, above all with up to 4, C atoms, such as mentioned above, and in particular methyl.

A lower alkoxy radical $R_{24}$ is especially a radical wherein the alkyl part has the above meaning, such as methoxy.

As suitable compounds of the formula XVI there should in particular be mentioned 5-(2-methylene-butyryl)-6-methyl-benzofurane-2-carboxylic acid, 5-(2-methylene-butyryl)-6-methoxy-benzofurane-2-carboxylic acid and 5-(2-methylenepropionyl)-6-methyl-benzofurane-2-carboxylic acid.

Particularly suitable benzofurane-2,3-dihydro-2-carboxylic acids are those of the formula XVII

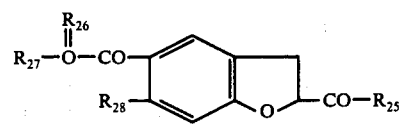

(XVII)

wherein $R_{25}$ is hydroxyl, alkoxy, cycloalkoxy or arylalkoxy, $R_{26}$ represents two hydrogen atoms or is lower alkylidene, $R_{27}$ is lower alkyl, $R_{28}$ is hydrogen, halogen, lower alkyl or lower alkoxy and $R_{29}$ is hydrogen or lower alkyl.

An alkoxy radical $R_{25}$ is especially a radical with 1-18, especially 1-12, C atoms, such as one of those mentioned above, such as, in particular, methoxy, ethoxy, n-butoxy, 2-hexyloxy and n-decyloxy.

A cycloalkoxy radical $R_{25}$ is especially a radical with 3-8, especially 5-7, ring C atoms and especially with up to 10, above all up to 8, C atoms, such as cyclopentyloxy and cyclohexyloxy.

An arylalkoxy radical $R_{25}$ is especially phenyl-lower alkoxy, wherein the lower alkyl part has the above meaning, such as benzyloxy.

A lower alkylidene radical $R_{26}$ is especially a radical with up to 7, especially up to 4, C atoms, such as methylene and ethylidene.

A lower alkyl radical $R_{27}$ is especially a radical with up to 7, especially up to 4, C atoms, such as, in particular, straight-chain radicals of this type, such as methyl, n-propyl, n-butyl and especially ethyl.

A halogen atom $R_{28}$ is bromine or iodine and especially fluorine or very particularly chlorine.

A lower alkyl radical $R_{28}$ or $R_{29}$ is especially a radical with up to 7, in particular with up to 4, C atoms, such as one of those mentioned above, and above all methyl.

A lower alkoxy radical $R_{28}$ is especially a radical with up to 7, in particular with up to 4, C atoms, such as one of those mentioned above, and above all methoxy.

Amongst the compounds of the formula XVII, those wherein $R_{25}$ is hydroxyl, $R_{26}$ is methylene or ethylidene, $R_{27}$ is straight-chain alkyl with 1-4 C atoms, $R_{28}$ is methyl, methoxy, chlorine or fluorine and $R_{29}$ is hydrogen or methyl, are particularly suitable.

Amongst the compounds of the formula XVII there should be singled out 5-(2-methylene-butyryl)-6-methyl-2,3-dihydrobenzofurane-2-carboxylic acid; 5-(2-methylene-butyryl)-6-fluoro-2,3-dihydro-benzofurane-2-carboxylic acid; 5-(2-methylene-butyryl)-6-chloro-2,3-dihydro-benzofurane-2-carboxylic acid; 5-(2-methylene-propionyl)-6-methyl-2,3-dihydro-benzofurane-2-carboxylic acid; 5-(2-methylene-hexanoyl)-6-methyl-2,3-dihydro-benzofurane-2-carboxylic acid; 5-(2-methylene-valeryl)-6-methyl-2,3-dihydro-benzofurane-2-carboxylic acid; 5-(2-methylenepropionyl)-6-methyl-2,3-dihydro-benzofurane-2-carboxylic acid; 5-(2-ethylidene-butyryl)-6-methyl-2,3-dihydro-benzofurane-2-carboxylic acid; 5-(2-methylenebutyryl)-6-methyl-2,3-dihydro-benzofurane-2-carboxylic acid methyl ester; 5-(2-methylenebutyryl)-6-methyl-2,3-dihydro-benzofurane-2-carboxylic acid ethyl ester; 5-(2-methylenebutyryl)-6-methyl-2,3-dihydro-benzofurane-2-carboxylic acid n-butyl ester; 5-(2-methylenebutyryl)-6-methyl-2,3-dihydro-benzofurane-2-carboxylic acid 2-hexyl ester; 5-(2-methylenebutyryl)-6-methyl-2,3-dihydro-benzofurane-2-carboxylic acid n-decyl ester; 5-(2-methylenebutyryl)-6-methyl-2,3-dihydro-benzofurane-2-carboxylic acid benzyl cyclohexyl ester; 5-(2-methylenebutyryl)-6-methyl)-2,3-dihydro-benzofurane-2-carboxylic acid cyclohexyl ester; 5-(2-methylenebutyryl)-6-methyl-2,3-dihydro-benzofurane-2-carboxylic acid benzyl ester; 5-(2-methylenebutyryl)-7-methyl-2,3-dihydrobenzofurane-2-carboxylic acid methyl ester; 5-(2-methylenebutyryl)-6-chloro-7-methyl-2,3-dihydro-benzofurane-2-carboxylic acid methyl ester; 5-(2-methylenepropionyl)-6-methyl-2,3-dihydro-benzofurane-2-carboxylic acid methyl ester; 5-(2-methylene-valeryl)-6-methyl-2,3-dihydro-benzofurane-2-carboxylic acid methyl ester; 5-(2-methylene-3-methyl-butyryl)-6-methyl-2,3-dihydro-benzofurane-2-carboxylic acid methyl ester and 5-(2methylenebutyryl)-6-fluoro2,3-dihydro-benzofurane-2-carboxylic acid methyl ester and particularly 5-(2-methylenebutyryl)-6,7-dimethyl-2,3-dihydro-benzofurane-2-carboxylic acid; 5-(2-methylene-3-methyl-2,3-dihydro-benzofurane-2-carboxylic acid and 5-(2-methylenebutyryl)-6-chloro-7-methyl-2,3-dihydro-benzofurane-2-carboxylic acid.

Particularly valuable pharmaceutical preparations are those which contain a compound of the formula Ig in which R', R", R''' and alk' have the meanings given, above all 1-[3-(o-chlorophenoxy)-2-hydroxypropyl]-4-(2-oxo-1-imidazolidinyl)-piperidine], 1-[3-(o-methoxyphenoxy)-2-hydroxypropyl]-4-(3-methyl-2-oxo-1-imidazolidinyl)-piperidine, 1-[3-o-chlorophenoxy)-2-hydroxypropyl]-4-(2-oxo-hexahydro-1-pyrimidinyl)-piperidine or particularly 1-[3-(o-methylphenoxy)-2-hydroxypropyl]-4-(2-oxo-hexahydro-1-pyrimidinyl)-piperidine, 1-[3-(o-methoxyphenoxy)-2-hydroxypropyl]-4-(2-oxo-hexahydro-1-pyrimidinyl)-piperidine, 1[3-(o-methylphenoxy)-2-hydroxypropyl]-4-(2-oxo-1-imidazolidinyl)-piperidine and especially 1-[3-(o-methoxyphenoxy)-2-hydroxypropyl]-4-(2-oxo-1-imidazolidinyl)-piperidine, together with 1,4-dihydrazinophthalazine sulphate, 2-benzyl-4,5-imidazoline hydrochloride, 2-[N-p-tolyl)-N-(m-oxyphenyl)-aminomethyl]-imidazoline hydrochloride, 1,2,3,4-tetrahydroisoquinoline-2-carboxamidine sulphate or especially together with 1-α-amino-α-methyl-β-(3,4-dihydroxyphenyl)-propionic acid or β-(1-azacyclooctyl)-ethylguanidine sulphate.

Very particularly valuable pharmaceutical preparations are those which contain 1-[3-(o-chlorophenoxy)-2-hydroxypropyl]-4-(2-oxo-1-imidazolidinyl)-piperidine, 1-[3-(o-methoxyphenoxy)-2-hydroxypropyl]-4-(3-methyl-2-oxo-1-imidazolidinyl)-piperidine, 1-[3-(o-chlorophenoxy)-2-hydroxypropyl]-4-(2-oxo-hexahydro-1-pyrimidinyl)-piperidine or particularly 1-[3-o-methylphenoxy)-2-hydroxypropyl]-4-(2-oxo-hexahydro-1-pyrimidinyl)-piperidine, 1-[3-(o-methoxyphenoxy)-2-hydroxypropyl]-4-(2-oxo-hexahydro-1-pyrimidinyl)-piperidine, 1-[3-(o-methylphenoxy)-2-hydroxypropyl]-4-(2-oxo-1-imidazolidinyl)-piperidine and especially 1-[3-(o-methoxyphenoxy)-2-hydroxpropyl]-4-(2-oxo-1-imidazolidinyl)-piperidine, together with 1-α-amino-α-methyl-β-(3,4-dihydroxyphenyl)-propionic acid or with β-(1-azacyclooctyl)-ethylguanidine sulphate.

Pharmaceutical preparations of very particular value are those which contain 1-{1-[3-(o-methoxy-phenoxy)-2-hydroxy-1-propyl]-piperidyl-(4)}-imidazolidinone-(2)together with 1-α-amino-α-methyl-β-(3,4-dihydroxyphenyl)-propionic acid or β-(1-azacyclooctyl)-ethylguanidine sulphate.

Amongst the pharmaceutical preparations which contain a compound of the formula I together with a diuretic, the following are particularly valuable:

Preparations which contain a compound of the formula Ig in which R', R", R''' and alk' have the meanings given, above all 1-[3-(o-chlorophenoxy)-2-hydroxypropyl]-4-(2-oxo-1-imidazolidinyl-piperidine, 1-[3-(o-methoxyphenoxy)-2-hydroxypropyl]-4-(3-methyl-2-oxo-1-imidazolidinyl)-piperidine, 1-[3-(o-chlorophenoxy)-2-hydroxypropyl]-4-(2-oxo-hexahydro-1-pyrimidinyl)-piperidine or particularly 1-[3-(o-methylphenoxy)-2-hydroxypropyl]-4-(2-oxo-hexahydro-1-pyrimidinyl)-piperidine, 1-[3-(o-methoxyphenoxy)-2-hydroxypropyl]-4-(2-oxo-hexahydro-1-pyrimidinyl)-piperidine, 1-[3-(o-methylphenoxy)-2-hydroxypropyl]-4-(2-oxo-1-imidazolidinyl)-piperidine and especially 1-[3-(o-methoxyphenoxy)-2-hydroxypropyl]-4-(2-oxo-1-imidazolidinyl)-piperidine, together with 6-chloro-7-sulphamyl-1,2,4-benzothiadiazine-1,1-diioxide, 6-trifluoromethyl-7- sulphamyl-1,2,4-benzothiadiazine-1,1-dioxide and 2-benzylthiomethyl-6-chloro-7-sulphamyl-1,2,4-benzothiadiazine-1,1-dioxide or together with 3-ethyl-6-chloro-7-sulphamyl-3,4-dihydro-1,2,4-benzothiadiazine-1,1-dioxide, 3-trichloromethyl-6-chloro-7-sulphamyl-3,4-dihydro-1,2,4-benzothiadiazine-1,1-dioxide, 3-benzyl-6-trifluoromethyl-7-sulphamyl-3,4-dihydro-1,2,4-benzothiadiazine-1,1-dioxide, 2-methyl-3-(2,2,2-trifluoroethylthiomethyl)-6-chloro-7-sulphamyl-3,4-dihydro-1,2,4-benzothiadiazine-1,1-dioxide, 3-(2,2,2-trifluoroethylthiomethyl)-6-chloro-7-sulphamyl-3,4-dihydro-1,2,4-benzothiadiazine-1,1-dioxide, 3-(5-norbornen-2-yl)-6-chloro-7-sulphamyl-3,4-dihydro-1,2,4-benzothiadiazine-1,1-dioxide, 2-methyl-3-chloromethyl-6-chloro-7-sulphamyl-3,4-dihydro-1,2,4-benzothiadiazine-1,1-dioxide, 6-chloro-7-sulphamyl-3,4-dihydro-1,2,4-benzothiadiazine-1,1-dioxide, 3-dichloromethyl-6-chloro-7-sulphamyl-3,4-dihydro-1,2,4-benzothiadiazine-1,1-dioxide, 3-cyclopentylmethyl-6-chloro-7-sulphamyl-3,4-dihydro-1,2,4-benzothiadiazine-1,1-dioxide, 6-trifluoromethyl-7-sulphamyl-3,4-dihydro-1,2,4-benzothiadiazine-1,1-dioxide or 3-isobutyl-6-chloro-7-sulphamyl-3,4-dihydro-1,2,4-benzothiadiazine-1,1dioxide or together with 2-chloro-5-N-methyl-sulphonamido-benzenesulphonamide; 2-chloro-5-N,N-dimethylsulphonamido-benzenesulphonamide; 2-chloro-5-piperidinosulphonyl-benzenesulphonamide; 2chloro-5-(N-carboxy-methyl-N-methyl)-sulphonamido-benzenesulphonamide; 2-chloro-5-(N-furfuryl-sulphonamido)-benzenesulphonamide; 2-chloro-5-(N-tetrahydrofurfuryl-sulphonamido)-benzenesulphonamide; 2-chloro-5-[N-methyl-N-(2-methyl-4-oxo-tetrahydrofurfuryl)-sulphonamido]-benzenesulphonamide; 4,5-dichlorobenzene-1,3-disulphonamide; 4-chloro-6-methylbenzene-1,3-disulphonamide; 4chloro-6-aminobenzene-1,3-disulphonamide; 2-chloro-5-methylsulphonyl-benzenesulphonamide; 2-chloro-5-ethylsulphonyl-benzenesulphonamide; 2-chloro-5-n-butylsulphonyl-benzenesulphonamide; 2-methyl-5-ethylsulphonyl-benzenesulphonamide; 2-methyl-5-methylsulphonyl-benzenesulphonamide; 2-methyl-5-n-butysulphonyl-benzenesulphonamide; 2-chloro-4-(N,N-dibenzylamino)-5-carboxyl-benzenesulphonamide; 2-furfuryl-amino-4-chloro-5-N(p-aminophenyl)-sulphamoyl-benzoic acid, 2-furfurylamino-4-chloro-5-N(o-aminophenyl)-sulphamoylbenzoic acid and particularly 3-sulphonamido-4-chloro-benzoic acid; 3-sulphonamido-4-chloro-benzamide; 3-(N-methylsulphamoyl)-4-chloro-N-methyl-benzamide; 1-chloro-4-[N-(2-methyltetrahydrofurfuryl)-sulphamoyl]benzenesulphonamide; 1,3-disulphamoyl-4-chlorobenzene; 2-chloro-5-[3-hydroxy-1-oxo-isoindolyl-(3)]-benzenesulphonamide; 2-ethyl-4-oxo-6-sulphamoyl-7-chloro-1,2,3,4-tetrahydro-quinazoline; 1-oxo-2-cyclohexyl-5-chloro-6-sulphamoyl-1,2-dihydroisoindole; 2-chloro-5-[N-(2,6-dimethylpiperidino)-carbamoyl]-benzenesulphonamide; 2-chloro-4-furfurylamino-5-carboxyl-benzenesulphonomide and 2-chloro-4-benzylamino-5-carboxyl-benzenesulphonamide or together with [2,3-dimethyl-4-(2-methylenebutyryl)-phenoxy]-acetic acid, [2-methyl-3-chloro-4-(2-methylene-butyryl)-phenoxy]-acetic acid, [4(2-methylenebutyryl)-1-naphthoxy]-acetic acid or [2,3-dichloro-4-(2-methylene-butyryl)-phenoxy]-acetic acid or together with 5-(2-methylene-butyryl)-6-methyl-benzofurane-2-carboxylic acid, 5-(2-methylene-butyryl)-6-methoxy-benzofurane-2-carboxylic acid or 5-(2-methylene-propionyl)-6-methyl-benzofurane-2-carboxylic acid or together with 5-(2-methylene-butyryl)-6-methyl-2,3-dihydro-benzofurane-2-carboxylic acid; 5-(2-methylene-butyryl)-6-fluoro-2,3-dihydrobenzofurane-2-carboxylic acid; 5-(2-methylenebutyryl)-6-chloro-2,3-dihydro-benzofurane-2-carboxylic acid; 5-(2-methylene-propionyl)-6-methyl-2,3-dihydrobenzofurane-2-carboxylic acid; 5-(2-methylene-hexanoyl)-6-methyl-2,3-dihydro-benzofurane-2-carboxylic acid; 5-(2-methylene-valeryl)-6-methyl-2,3-dihydrobenzofurane-2-carboxylic acid; 5-(2-methylenepropionyl)-6-methyl-2,3-dihydrobenzofurane-2-carboxylic acid; 5-(2-ethylidene-butyryl)-6-methyl-2,3-dihydrobenzofurane-2-carboxylic acid; 5-(2-methylenebutyryl)-6-methyl-2,3-dihydro-benzofurane-2-carboxylic acid methyl ester; 5-(2-methylenebutyryl)-6-methyl-2,3-dihydro-benzofurane-2-carboxylic acid ethyl ester; 5-(2-methylenebutyryl)-6-methyl-2,3-dihydro-benzofurane-2-carboxylic acid n-butyl ester; 5-(2-methylenebutyryl)-6-methyl-2,3-dihydro-benzofurane-2-carboxylic acid 2-hexyl ester; 5-(2-methylenebutyryl)-6-methyl-2,3-dihydro-benzofurane-2-carboxylic acid n-decyl ester; 5-(2-methylene-butyryl)-6-methyl-2,3-dihydro-benzofurane-2-carboxylic acid cyclopentyl ester; 5-(2-methylenebutyryl)-6-methyl-2,3-dihydrobenzofurane-2-carboxylic acid cyclohexyl ester; 5-(2-methylenebutyryl)-6-methyl-2,3-dihydro-benzofurane-2-carboxylic acid benzyl ester; 5-(2-methylenebutyryl)-7-methyl-2,3-dihydro-benzofurane-2-carboxylic acid methyl ester; 5-(2-methylenebutyryl)-6-chloro-7-methyl-2,3-dihydro-benzofurane-2-carboxylic acid methyl ester; 5-(2-methylenepropionyl)-6-methyl-2,3-dihydrobenzofurane-2-carboxylic acid methyl ester; 5-(2-methylene-valeryl)-6-methyl-2,3-dihydro-benzofurane-2-carboxylic acid methyl ester; 5-(2-methylene-3-methyl-butyryl)-6-methyl-2,3-dihydro-benzofurane-2-carboxylic acid methyl ester; and 5-(2-methylenebutyryl)-6-fluoro-2,3-dihydro-benzofurane-2-carboxylic acid methyl ester and particularly 5-(2-methylenebutyryl)-6,7-dimethyl-2,3-dihydro-benzofurane-2-carboxylic acid; 5-(2-methylene-3-methyl-butyryl)-6-methyl-2,3-dihydro-benzofurane-2-carboxylic acid; 5-(2-methylenebutyryl)-6-chloro-7-methyl-2,3-dihydro-benzofurane-2-carboxylic acid.

Pharmaceutical preparations of particular value are those which contain 1-[3-(o-chlorophenoxy)-2-hydroxypropyl]-4-(2-oxo-1-imidazolidinyl)-piperidine, 1-[3-(o-methoxyphenoxy)2-hydroxypropyl]-4-(3-methyl-2-oxo-1-imidazolidinyl)-piperidine, 1-[3-(o-chlorophenoxy)-2-hydroxypropyl]-4-(2-oxo-hexahydro-1-pyrimidinyl)-piperidine or particularly 1-[3-(o-methylphenoxy)-2-hydroxypropyl]-4-(2-oxo-hexahydro-1-pyrimidinyl)-piperidine, 1-[3-(o-methoxyphenoxy)-2-hydroxypropyl]-4-(2-oxo-hexahydro-1-pyrimidinyl)-piperidine, 1-[3-(o-methylphenoxy)-2-hydroxypropyl]-4-(2-oxo-1-imidazolidinyl)-piperidine and especially 1-[3-(o-methoxyphenoxy)-2-hydroxypropyl]-4-(2-oxo-1-imidazolidinyl)-piperidine, together with 6-chloro-7-sulphamyl-1,2,4-benzothiadiazine-1,1-dioxide, 6-trifluoromethyl-7-sulphamyl-1,2,4-benzothiadiazine-1,1-dioxide or 2-benzylthiomethyl-6-chloro-7-sulphamyl-1,2,4-benzothiadiazine-1,1-dioxide or together with 2-methyl-3-chloromethyl-6-chloro-7-sulphamyl-3,4-dihydro-1,2,4-benzothiadiazine-1,1-dioxide, 6-chloro-7-sulphamyl-3,4-dihydro-1,2,4-benzothiadiazine-1,1-dioxide, 3-dichloro-methyl-6-chloro-7-sulphamyl-3,4-dihydro-1,2,4-benzothiadiazine-1,1-dioxide or 3-isobutyl-6-chloro-7-sulphamyl-3,4-dihydro-1,2,4-benzothiadiazine-1,1-dioxide or together with 3-sulphonamido-4-chloro-benzoic acid, 3-sulphonamido-4-chloro-benzamide, 3-(N-methylsulphamoyl)-4-chloro-N-methylbenzamide, 1-chloro-4-[N-methyl-N-(2-methyltetrahydrofurfuryl)-sulphamoyl]-benzenesulphonamide, 2-chloro5-[3-hydroxy-1-oxo-isoindolyl-(3)]-benzenesulphonamide, 2-ethyl-4-oxo-6-sulphamoyl-7-chloro-1,2,4-tetrahydroquinazoline, 1-oxo-2-cyclohexyl-5-chloro-6-sulphamoyl-1,2-dihydroisoindole, 2-chloro-5-[N-(2,6-dimethylpiperidino)-carbamoyl]-benzenesulphonamide, 2-chloro-4-furfurylamino-5-carboxyl-benzenesulphonamide or 2-chloro-4-benzylamino-5-carboxyl-benzenesulphonamide, or together with [2,3-dimethyl-4-(2-methylene-butyryl)-phenoxy]-acetic acid, [2-methyl-3-chloro-4-(2-methylene-butyryl)-phenoxy]-acetic acid, [4-(2-methylene-butyryl)-1-naphthoxy]-acetic acid or [2,3-dichloro-4-(2-methylene-butyryl)-phenoxy]-acetic acid or together with 5-(2-methylene-butyryl)-6,7-dimethyl-2,3-dihydro-benzofurane-2-carboxylic acid, 5-(2-methylene-3-methyl-butyryl)-6-methyl-2,3-dihydro-benzofurane-2-carboxylic acid or 5-(2-methylene-butyryl)-6-chloro-7-methyl-2,3-dihydrobenzofurane-2-carboxylic acid or together with 5-(2-methylenebutyryl)-6-methyl-benzofurane-2-carboxylic acid, 5-(2-methylene-butyryl)-6-methoxy-benzofurane- 2-carboxylic acid or 5-(2-methylene-propionyl)-6-methyl-benzofurane-2-carboxylic acid.

A very particular subject of the invention are pharmaceutical preparations which contain 1-{1-[3-(o-methoxyphenoxy)-2-hydroxy-1-propyl]-piperidyl-(4)}-imidazolidinone(2) together with 1-oxo-3-(3-sulphamyl-4-chloro-phenyl)-3-hydroxyisoindoline, 6-chloro-7-sulphamyl-3,4-dihydro-1,2,4-benzothiadiazine-1,1-dioxide, 3-cyclopentylmethyl-6-chloro-7-sulphamyl-3,4-dihydro-1,2,4-benzothiadiazine-1,1-dioxide or 5-(2-methylenebutyryl)-6-methyl-benzofurane-2-carboxylic acid.

In the pharmaceutical preparations the active ingredients may be in their free form or in the form of their salts, if any.

The examples which follow explain the invention without, however, limiting it.

EXAMPLE 1

A solution of 10 g of 1-(o-methoxy-phenoxy)-2,3-epoxypropane and 10 g of 1-[piperidyl-(4)]-imidazolidinone-(2) in 50 ml of ethanol is warmed to 80° C for 4 hours and then evaporated in vacuo. The residue is dissolved in 100 ml of 2 N hydrochloric acid, the solution is extracted with ether and the aqueous phase is rendered alkaline by adding 10 N sodium hydroxide solution. 1-{1-[3-(o-Methoxy-phenoxy)-2-hydroxy-1-propyl]-piperidyl-(4)}-imidazolidinone-(2) separates out and after recrystallisation from ethanol melts at 138° C. The hydrochloride melts at 158°–160° C.

1-[Piperidyl-(4)]-imidazolidinone-(2) used as the starting material can be manufactured as follows:

55 g of β-chloroethyl isocyanate are added dropwise to a solution of 47 g of 4-aminopyridine in 200 ml of dimethylformamide and the mixture is stirred for 1 hour. On adding 400 ml of water, N-(4-pyridyl)-N'-β-chloroethylurea precipitates and after recrystallisation from alcoholwater melts at 120°–122° C.

66 g of N-(4-pyridyl)-N'-β-chloroethyl-urea are heated with a solution of 12 g of sodium ethylate in 400 ml of ethanol under reflux for 2 hours. 1-(4-Pyridyl)-imidazolidinone-(2) precipitates, and melts at 205°–206° C.

15 g of 1-(4-pyridyl)-imidazolidinone-(2) in 150 ml of alcohol are hydrogenated in the presence of 1.5 g of ruthenium on charcoal (10 percent strength) at 150° C and under a pressure of 150 atmospheres gauge pressure. After the absorption of hydrogen has ceased, the catalyst is filtered off, the filtrate is evaporated to dryness and the residue is recrystallised from methylene chloride/petroleum ether. 1-[Piperidyl-(4)]-imidazolidinone-(2) is obtained in crystals of melting point 154°–158° C.

EXAMPLE 2

15 g of 1-(m-methoxy-phenoxy)-2,3-epoxy-propane and 15 g of 1-[piperidyl-(4)]-imidazolidinone-(2) in 30 ml of ethanol are warmed to 80° C for 4 hours and the mixture is then evaporated in vacuo. The residue is treated with 100 ml of 2 N hydrochloric acid and extracted with ether. The aqueous layer is then reduced alkaline by adding 10 N sodium hydroxide solution and is extracted with methylene chloride. After evaporation of the solvent, 1-{1-[3-(m-methoxy-phenoxy)-2-hydroxy-1-propyl]-piperidyl-(4)}-imidazolidinone-(2) is obtained as a viscous oil of which the fumarate melts at 192°–193° C.

EXAMPLE 3

A solution of 15 g of 1-(p-allyloxy-phenoxy)-2,3-epoxy-propane and 15 g of 1-[piperidyl-(4)]-imidazolidinone-(2) in 30 ml of alcohol is warmed to 90° C for 4 hours and subsequently evaporated in vacuo. The residue is dissolved in 2 N hydrochloric acid, the solution is extracted with ether and 10 N sodium hydroxide solution is added to the aqueous phase until it gives an alkaline reaction. After extraction with methylene chloride and evaporation of the solvent, 1-{1-[3-(p-allyloxy-phenoxy)-2-hydroxy-1-propyl]-piperidyl(4)}-imidazolidinone-(2) is left; after recrystallisation from ethanol it melts at 132°–3° C. The methanesulphonate melts at 154°–157° C.

EXAMPLE 4

10 g of 1-{1-[3-(p-benzyloxy-phenoxy)-2-hydroxy-1-propyl)-piperidyl-(4)}-imidazolidinone-(2) in 200 ml of methanol are hydrogenated in the presence of 1 g of palladium on charcoal (5 percent strength) at room temperature and under normal pressure. After the hydrogen uptake has ceased, the catalyst is filtered off and the solvent is evaporated. 1-{1-[3-(p-Hydroxy-phenoxy)-2-hydroxy-1-propyl)-piperidyl-(4)}imidazolidinone-(2) is left; its hydrochloride melts at 238° C.

In analogous manner, the hydrogenation of 1-[3-(o-benzyloxyphenoxy)-2-hydroxypropyl]-4-(2-oxo-1-imidazolidinyl)-piperidine yields the 1-[3-(o-hydroxy-phenoxy)-2-hydroxypropyl]-4-(2-oxo-1-imidazolidinyl)-piperidine, which melts at 183°–185° C.

EXAMPLE 5

Warming 15 g of 1-(p-benzyloxy-phenoxy)-2,3-epoxypropane and 15 g of 1-(4-piperidyl)-2-imidazolidinone in 30 ml of ethanol to 80° C and subsequently evaporating the solvent yields 1-{1-[3-(p-benzyloxyphenyl)-2-hydroxy-1-propyl)-piperidyl-(4)}-imidazolidinone-(2), which melts at 166° C.

The 1-[3-(o-benzyloxy-phenoxy)-2-hydroxypropyl]-4-(2-oxo-1-imidazolidinyl)-piperidine can be manufactured in analogous manner.

EXAMPLE 6

A mixture of 15 g of 1-(p-acetamino-phenoxy)-2,3-epoxy-propane, 15 g of 1-(4-piperidyl)-2-imidazolidinone and 30 ml of alcohol is warmed to 80° C for 3 hours and then evaporated in vacuo. The residue is dissolved in 2 N hydrochloric acid and extracted with ether, and the aqueous phase is then rendered alkaline by adding 10 N sodium hydroxide solution. 1-{1-[3-(p-Acetamido-phenoxy)-2-hydroxy-1-propyl]-piperidyl(4)}-imidazolidinone-(2) precipitates and after recrystallisation from ethanol melts at 162°–165° C. The hydrochloride melts at 257°–259° C.

EXAMPLE 7

A mixture of 15 g of 1-(o-allyl-phenoxy)-2,3-epoxy-propane, 15 g of 1-(4-piperidyl)-2-imidazolidinone and 30 ml of alcohol is warmed to 80° C for 4 hours and subsequently evaporated. The residue is dissolved in 200 ml of 2 N hydrochloric acid and extracted with ether, and the aqueous phase is then rendered alkaline by adding 10 N sodium hydroxide solution. 1-{1-[3-(o-Allyl-phenoxy)-2-hydroxy-1-propyl]-piperidyl-(4)}-imidazolidinone-(2) separates out as an oil. The hydrochloride melts at 186°–189° C.

EXAMPLE 8

A mixture of 15 g of 1-(o-allyloxy-phenoxy)-2,3-epoxy-propane, 15 g of 1-(4-piperidyl)-2-imidazolidinone and 45 ml of ethanol is warmed to 90° C for 4 hours and then evaporated in vacuo. The residue is dissolved in 200 ml of 2 N hydrochloric acid, the solution is extracted with ether and the aqueous phase is then rendered alkaline by adding concentrated sodium hydroxide solution. The 1-{1-[3-(o-allyloxyphenoxy)-2-hydroxy-1-propyl]-piperidyl-(4)}-imidazolidinone-(2) which has precipitated is extracted by shaking with methylene chloride. The oil which remains after drying and evaporating the methylene chloride is dissolved in 44 ml of ethanol. After adding 10.5 g of cyclohexylsulphamic acid, crystals of the cyclohexylsulphamate separate out; these melt at 128°–130° C after recrystallisation from ethanol.

EXAMPLE 9

A solution of 30 g of 1-(o-methoxy-phenoxy)-2,3-epoxypropane and 30 g of 1-[piperidyl-(4)]-3-methyl-imidazolidinone in 100 ml of ethanol is warmed to 90° C for 3 hours and evaporated in vacuo. The residue is dissolved in 100 ml of 2 N hydrochloric acid, the solution is extracted with ether and the aqueous phase is rendered alkaline by adding 10 N sodium hydroxide solution. After extraction with methylene chloride and evaporation of the solvent, 1-{1-[3-(o-methoxy-phenoxy)-2-hydroxy-1-propyl]-piperidyl-(4)}-3-methyl-imidazolidinone-(2) remains as an oil. After recrystallisation from ethanol/ether, the hydrochloride melts at 172° C.

1-[Piperidyl-(4)]-3-methyl-imidazolidinone, required as the starting material, can be manufactured by hydrogenation of 1-(4-pyridyl)-3-methyl-imidazolidinone-(2) with ruthenium as the catalyst. The compound melts at 60°–64° C.

EXAMPLE 10

Analogously to the description in Example 1, 1-(p-N-methylcarbamoyl-phenoxy)-2,3-epoxy-propane and 1-[piperidyl-(4)]-imidazolidinone-(2) yield 1-{1-[3-(p-N-methylcarbamoylphenoxy)-2-hydroxy-1-propyl]-piperidyl-(4)}-imidazolidinone-(2), which after recrystallisation from ethyl acetate melts at 180°–182° C, and of which the neutral fumarate, after recrystallisation from methanol/ether melts at 191°–196° C.

EXAMPLE 11

Analogously to the description in Example 1, 1-(o-methyl-phenoxy)-2,3-epoxy-propane and 1-[piperidyl-(4)]-imidazolidinone-(2) yield 1-{1-[3-(o-methyl-phenoxy)-2-hydroxy-1-propyl]-piperidyl-(4)}-imidazolidinone-(2) of melting point 114°–116° C.

EXAMPLE 12

Analogously to the description in Example 1, 1-(o-chloro-phenoxy)-2,3-epoxy-propane and 1-[piperidyl-(4)]-imidazolidinone-(2) yield 1-{1-[3-(o-chloro-phenoxy)-2-hydroxy-1-propyl]-piperidyl-(4)}-imidazolidinone-(2) of melting point of 150°–151° C, of which the neutral fumarate, when recrystallised from methanol/ether, melts at 172°–173° C (sintering from 170° C onwards).

EXAMPLE 13

Analogously to the description in Example 1, 1-(2-methoxy-4-N-methylcarbamoyl-phenoxy)-2,3-epoxy-propane and 1-[piperidyl-(4)]-imidazolidinone-(2) yield 1-{1-[3-(2-methoxy-4-N-methylcarbamoyl-phenoxy)-2-hydroxy-1-propyl]-piperidyl-(4)}-imidazolidinone-(2) which after recrystallisation from isopropanol melts at 104°–107° C.

EXAMPLE 14

A solution of 6.56 g of 1-(o-tolyloxy)-2,3-epoxy-propane and 7.7 g of 1-[piperidyl-(4)]-2-oxo-hexahydro-pyrimidine in 5 ml of ethanol is heated of 3½ hours at a bath temperature of 95° C and then evaporated in vacuo. The residue is triturated with ethyl acetate, whereupon crystallisation commences. The crystals are stirred with water and filtered off. Recrystallisation from ethyl acetate/petroleum ether yields the 1-[3-(o-tolyloxy)-2-hydroxy-propyl]-4-(2-oxo-hexahydro-1-pyrimidinyl)-piperidine which melts at 145°–147° C.

The 1-[piperidyl-(4)]-2-oxo-hexahydro-pyrimidine used as starting material can be prepared as follows:

At room temperature, 30 g of γ-chloro-propyl-isocyanate are added dropwise over the course of 2 hours to a solution of 18.8 g of 4-amino-pyridine in 80 ml of dimethyl formamide and stirring is continued for 24 hours. After the dimethyl formamide has been evaporated off in a water jet vacuum at 80° C, 4.27 g of the residue are dissolved in 25 ml of methanol and this solution is treated at boiling heat over the course of 20 minutes with a solution of 1.19 g of sodium methylate in 25 ml of methanol with stirring. The reaction mixture is then refluxed for 1 hour. The precipitated sodium chloride is filtered off, the filtrate is evaporated in vacuo and the residue is recrystallised from chloroform/petroleum ether to yield the 1-[pyridyl-(4)]-2-oxo-hexahydro-pyrimidine which melts at 180°–182° C.

17.7 g of 1-[pyridyl-(4)]-2-oxo-hexahydro-pyrimidine are hydrogenated in 180 ml of water in the presence of 2.5 g of ruthenium on charcoal catalyst (10%) at 120° C and an atmospheric excess pressure of 120. After the uptake of hydrogen has ceased, the catalyst is filtered off and the filtrate is evaporated to dryness. Recrystallisation from chloroform/petroleum ether yields the 1-[piperidyl-(4)]-2-oxo-hexahydro-pyrimidine (m.p. 207°–210° C).

EXAMPLE 15

A solution of 9 g of 1-(o-methoxy-phenoxy)-2,3-epoxypropane and 9.15 g of 1(4-piperidyl)-2-oxo-hexahydro-pyrimidine in 7 ml of abs. ethanol is heated for 5 hours to 95° C and then evaporated in vacuo. The residue is recrystallised from ethyl acetate/petroleum ether to yield the 1-[3-(o-methoxyphenoxy)-2-hydroxypropyl]-4-(2-oxo-hexahydro-1-pyrimidinyl)-piperidine, which melts at 130°–133° C.

A solution of 17.1 g of the above base in 100 ml of abs. ethanol is added to a solution of 5.5 g of furamic acid in 105 ml of abs. ethanol. The 1-[3-(o-methoxyphenoxy)-2-hydroxypropyl]-4-(2-oxo-hexahydro-1-pyrimidinyl)-piperidine fumarate (1:1) precipitates on the addition of ether; m.p. 149°–151° C.

EXAMPLE 16

A solution of 10.4 g of 1-[p-(2-methoxyethyl)-phenoxy]-2,3-epoxy-propane and 9.15 g of 1-(4-piperidyl)-2-oxo-hexahydropyrimidine in 7 ml of abs. ethanol is heated for 5 hours to 95° C and then evaporated in vacuo. The residue is recrystallised from ethyl acetate/petroleum ether to yield the 1-[3-(p-(2-methoxyethyl)- phenoxy)-2-hydroxypropyl]4-(2-oxo-hexahydro-1-pyrimidinyl)-piperidine, which melts at 113°–115° C.

A solution of 18.5 g of the base described above in 30 ml abs. ethanol is added to a solution of 5.5 g of furmaric acid in 105 ml of absolute ethanol. The 1-[3-(p-(2-methoxyethyl)-phenoxy)-2-hydroxypropyl]- 4-(2-oxo-hexahydro-1-pyrimidinyl)-piperidine fumarate (2:1) precipitates on the addition of ether; m.p. 157°–159° C.

Example 17

A solution of 19.35 g of 1-(p-acetamido-phenoxy)-2,3-epoxy-propane and 9.15 g of 1-(4-piperidyl)-2-oxo-hexahydropyrimidine in 10 ml of abs. ethanol is heated to 95° C. The reaction product crystallises out at boiling heat after about 5 minutes. The crystal broth is diluted with 10 ml of abs. ethanol and heated for a further 5 hours. When the reaction is terminated the batch is evaporated in vacuo and the residue is recrystallised from abs. ethanol/ether to yield the 1-[3-(p-acetamido-phenoxy)-2-hydroxypropyl]-4-(2-oxo-hexahydro-1-pyrimidinyl)-piperidine, which melts at 218°–221° C.

EXAMPLE 18

A solution of 9.2 g of 1-(o-chloro-phenoxy)-2,3-epoxy-propane and 9.15 g of 1-(4-piperidyl)-2-oxo-hexahydro-pyrimidine in 7 ml of abs. ethanol is heated for 5 hours to 95° C and then evaporated in vacuo. The residue is recrystallised from chloroform/petroleum ether to yield the 1-[3-(o-chloro-phenoxy)-2-hydroxypropyl]-4-(2-oxo-hexahydro-1-pyrimidinyl)-piperidine, which melts at 150°–153° C.

A solution of 12.7 g of the above base in 60 ml of abs. ethanol is added to a solution of 4.05 g of furmaric acid in 77 ml of abs. ethanol. The 1-[3-(o-chlorophenoxy)-2-hydroxypropyl]-4-(2-oxo-hexahydro-1-pyrimidinyl)-piperidine fumarate (2:1) precipitates on the addition of ethyl acetate and ether; m.p. 169°–171° C.

EXAMPLE 19

A solution of 10.3 g of 1-(o-allyloxy-phenoxy)-2,3-epoxy-propane and 9.15 g of 1-(1-(4-piperidyl))-2-oxo-hexahydropyrimidine in 7 ml abs. ethanol is heated for 5 hours to 95° C and then evaporated in vacuo. The residue is recrystallised from isopropanol to yield the 1-[3-(o-allyloxy-phenoxy)-2-hydroxypropyl]-4-(2-oxo-hexahydro-1-pyrimidinyl)-piperidine, which melts at 122°–125°C.

A solution of 8.45 g of the above base in 50 ml of abs. ethanol is added to a solution of 2.52 g of fumaric acid in 50 ml of abs. ethanol. The 1-[3-o-allyloxy-phenoxy)-2-hydroxypropyl]-4-(2-oxo-hexahydro-1-pyrimidinyl)-piperidine fumarate (1:1) precipitates on addition of ether; m.p. 154°–156° C.

EXAMPLE 20

A solution of 10.8 g of 1(p-methoxy-phenoxy)-2,3-epoxypropane and 10.15 g of 1-(4-piperidyl)-imidazolidin-(2)-one in 10 ml of abs. ethanol is heated for 5 hours to 95° C and then evaporated in vacuo. The residue is dissolved in 80 ml of 2 normal hydrochloric acid. Extraction is performed with methylene chloride and the aqueous phase is then made alkaline by addition of a concentrated aqueous sodium hydroxide solution. Extraction with methylene chloride and then evaporation of the solvent yields the 1-[3-(p-methoxy-phenoxy)-2-hydroxypropyl]-4-(2-oxo-1-imidazolidinyl)-piperidine, which melts at 148°–150° C after recrystallisation form isopropanol.

13.7 g of the above base are dissolved in 40 ml of abs. ethanol by warming. The solution is added to 20.7 ml of a 1.9 N ethanolic solution of hydrochloric acid. The 1-[3-(p-Methoxyphenoxy)-2-hydroxypropyl]-4-(2-oxo-1-imidazolidinyl)-piperidine hydrochlorid precipitates on cooling. It melts at 209°–211° C.

EXAMPLE 21

A solution of 0.50 g of 1-[3-(o-hydroxy-phenoxy)-2-hydroxypropyl]-4-(2-oxo-1-imidazoldinyl)-piperidine in 20 ml of dimethylformamide is treated with 65 mg of sodium hydride suspension (55% in paraffin oil) and the mixture is stirred for 1 hour at 20°–30° C. Then 0.23 g of methyl idoide is added and the reaction mixture is stirred for 18 hours at 20°–30° C. The solvent is evaporated off in vacuo and the residue is then washed with 5 ml of pentane. The undissolved substance is partitioned between 30 ml of ethyl acetate and 3 ml of 6 normal sodium hydroxide solution. The organic phase is extracted once more with 3 ml of 6 normal sodium hydroxide solution, dried over magnesium sulphate and evaporated in vacuo, to yield 0.45 g of a yellow oil. Recrystallisation from ethanol yields pure 1-[3-(o-methoxyphenoxy)-2-hydroxypropyl]-4-(2-oxo-1-imidazolidinyl)-piperidine with a melting point of 138° C (melting point of the hydrochloride: 158°–160° C). Thin-layer chromatography shows the product to be identifical with that described in Example 1.

EXAMPLE 22

Tablets containing 25 mg of 1-{1-[3-(o-methoxy-phenoxy)2-hydroxy-1-propyl]-piperidyl-(4)}-imidazolidinone-(2) can, for example, be manufactured to have the following composition:

| Composition | |
|---|---|
| 1-{1-[3-(o-Methoxy-phenoxy)-2-hydroxy-1-propyl]-piperidyl(4)}-imidazolidinone-(2) | 25.0 mg |
| Lactose | 34.0 mg |
| Wheat starch | 30.0 mg |
| Colloidal silica | 5.0 mg |
| Talc | 5.0 mg |
| Magnesium stearate | 1.0 mg |
| | 100.0 mg |

MANUFACTURE

The active compound is mixed with the lactose, the colloidal silica and a part of the wheat starch and the mixture is forced through a sieve. A further part of the wheat starch is worked into a paste with a 5-fold amount of water on a water bath and the powder mixture is kneaded with this paste until a slightly plastic mass has been produced.

The mass is forced through a sieve and dried and the dry granules are again sieved. Thereafter, the remaining wheat starch, the talc and the magnesium stearate are mixed in and the mixture is pressed to give tablets weighing 100 mg, having a breaking groove.

EXAMPLE 23

Tablets containing 15 mg of 1-{1-[3-(o-methoxy-phenoxy)-2-hydroxy-1-propyl]-piperidyl-(4)}-imidazolidinone-(2) and 10 mg of β-(1-azacyclooctyl)-ethylguanidine sulphate.

| Composition | |
|---|---|
| 1-{1-[3-(o-Methoxy-phenoxy)-2-hydroxy-1- | |

-continued

| Composition | |
|---|---|
| propyl]-piperidyl-(4)}-imidazolidinone-(20) | 15.0 mg |
| β-(1-Azacyclooctyl)-ethyl-guanidine sulphate | 10.0 mg |
| Lactose | 34.0 mg |
| Wheat starch | 30.0 mg |
| Colloidal silica | 5.0 mg |
| Talc | 5.0 mg |
| Magnesium stearate | 1.0 mg |
| | 100.0 mg |

MANUFACTURE

The active compound is mixed with the lactose, the colloidal silica and a part of the wheat starch and the mixture is forced through a sieve. A further part of the wheat starch is worked into a paste with a 5-fold amount of water on a water bath and the powder mixture is kneaded with this paste until a slightly plastic mass has been produced.

The mass is forced through a sieve and dried and the dry granules are again sieved. Thereafter, the remaining wheat starch, the talc and the magnesium stearate are mixed in and the mixture is pressed to give tablets weighing 100 mg, having a breaking groove.

EXAMPLE 24

Tablets containing 25 mg of 1-{1-[3-(o-methoxyphenoxy)-2-hydroxy-1-propyl]-piperidyl-(4)}-imidazolidinone-(2) and 25 mg of 6-chloro-7-sulphamyl-3,4-dihydro-1,2,4-benzothiadiazine-1,1-dioxide.

| Composition | |
|---|---|
| 1-{1-[3-(o-Methoxy-phenoy)-2-hydroxy-1-propyl]-piperidyl-(4)}-imidazolidinone-(2) | 25.0 mg |
| 6-Chloro-7-sulphamyl-3,4-dihydro-1,2,4-benzothiadiazine-1,1-dioxide | 25.0 mg |
| Lactose | 34.0 mg |
| Wheat starch | 30.0 mg |
| Colloidal silica | 5.0 mg |
| Talc | 5.0 mg |
| Magnesium stearate | 1.0 mg |
| | 125.0 mg |

MANUFACTURE

The active compound is mixed with the lactose, the collodial silica and a part of the wheat starch and the mixture is forced through a sieve. A further part of the wheat starch is worked into a paste with a 5-fold amount of water on a water bath and the powder mixture is kneaded with this paste until a slightly plastic mass has been produced.

The mass is forced through a sieve and dried and the dry granules are again sieved. Thereafter, the remaining wheat starch, the talc and the magnesium stearate are mixed in and the mixture is pressed to give tablets weighing 125 mg, having a breaking groove.

EXAMPLE 25

Tablets containing 25 mg of 1-[3-(o-methoxyphenoxy)-2-hydroxypropyl]-4-(2-oxo-hexahydro-1-pyrimidinyl)-piperidine can be manufactured e.g. in the following composition:

| Composition | |
|---|---|
| 1-[3-(o-methoxyphenoxy-2-hydroxypropyl]-4-(2-oxo-hexahydro-1-pyrimidinyl)-piperidine | 250 mg |
| lactose | 34.0 mg |
| wheat starch | 30.0 mg |
| colloidal silicic acid | 5.0 mg |
| talcum | 5.0 mg |
| magnesium stearate | 1.0 mg |
| | 100.0 mg |

MANUFACTURE

The active substance is mixed with the lactose, the colloidal silicic acid and a portion of the wheat starch and the mixture is passed through a sieve. A further portion of the wheat starch is pasted on a water bath with the 5-fold amount of water and the powder mixture is kneaded with the resulting paste until a slightly plastic mass is obtained. This mass if forced through a sieve, dried, and the dry granules are then sieved. The remainder of the wheat starch, the talcum and the magnesium stearate are then admixed and the mixture is pressed into tablets weighing 100 mg with breaking notch.

EXAMPLE 26

Tablets containing 15 mg of 1-[3-(o-tolyloxy)-2-hydroxypropyl]-4-(2-oxo-hexahydro-1-pyrimidinyl)-piperidine and 10 mg of β-(1-azacyclooctyl)-ethyl-guanidine sulphate can be manufacture e.g. in the following composition:

| Composition | |
|---|---|
| 1-[3-(o-tolyloxy)-2-hydroxypropyl]-4-(2-oxo-hexahydro-1-pyrimidinyl)-piperidine | 15.0 mg |
| β-(1-azacyclooctyl)-ethyl-guanidine sulphate | 10.0 mg |
| lactose | 34.0 mg |
| wheat starch | 30.0 mg |
| colloidal silicic acid | 5.0 mg |
| talcum | 5.0 mg |
| magnesium stearate | 1.0 mg |
| | 100.0 mg |

Tablets weighing 100 mg with breaking notch are manufactured by carrying out the procedure as described in Example 25.

EXAMPLE 27

Tablets containing 25 mg of 1-[3-(o-methoxyphenoxy)2-hydroxypropyl]-4-(2-oxo-hexahydro-1-pyrimidinyl)-piperdine can be manufactured e.g. in the following composition:

| Composition | |
|---|---|
| 1-[3-(o-methoxyphenoxy)-2-hydroxy-propyl]-4-(2-oxo-hexahydro-1-pyrimidinyl)-piperidine | 25.0 mg |
| 6-chloro-7-sulphamyl-3,4-dihydro-1,2,4-benzothiadiazine-1,1-dioxide | 25.0 mg |
| lactose | 34.0 mg |
| wheat starch | 30.0 mg |
| colloidal silicic acid | 5.0 mg |
| talcum | 5.0 mg |
| magnesium stearate | 1.0 mg |
| | 125.0 mg |

Tablets weighing 125 mg with breaking notch are manufactured by carrying out the procedure as described in Example 25.

We claim:

1. A pharmaceutical composition useful in treating hypertension and tachycardia which comprises an antihypertensively and anti-tachycardially effective amount of a piperidine compound having the formula

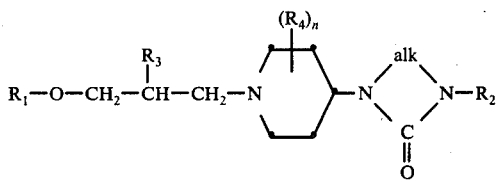

wherein R₁ is phenyl, naphthyl, 5,6,7,8-tetrahydro-1-naphthyl or 5,6,7,8-tetrahydro-2-naphthyl radical which is unsubstituted, monosubstituted or disubstituted by lower alkyl, lower alkoxy, lower alkenyl, lower alkenyloxy, halogen, halogeno-lower alkyl, carbamoyl, lower alkyl-substituted carbamoyl, lower alkoxycarbonylamino-lower alkyl, lower alkoxy-lower alkoxy, lower alkanoylaminoethenyl, lower alkylthio-lower alkoxy, hydroxyl, lower alkanoyl, lower alkoxylower alkyl, lower alkynyl, lower alkylthio-lower alkyl, hydroxy-lower alkyl, lower alkanoyloxy, lower alkylthio, lower alkanoyl amino, cyano, amino, nitro, ureido, lower alkylated ureido, phenyl-lower alkoxy, or lower alkynyloxy, R₂ is hydrogen, lower alkyl, lower alkenyl, α-phenyl-lower alkyl or lower alkanoyl, R₃ is a free hydroxyl group, a lower alkanoyloxy group or a lower alkoxy group, R₄ is hydrogen or lower alkyl, n is an integer from 0 to 4, and alk is an optionally mono-lower alkylated ethylene radical or a salt thereof, together with a therapeutically useful carrier.

2. The pharmaceutical composition of claim 1, wherein the active compound has the formula defined in claim 1, wherein R₁ is a phenyl radical mono- or di-substituted by lower alkyl, lower alkoxy, lower alkenyl, lower alkenyloxy, lower alkanoyl, lower alkanoylamino, hydroxyl, benzyloxy, N-lower alkylcarbamoyl or halogen, R₂ is hydrogen or lower alkyl, R₃ is hydroxyl, R₄ is hydrogen or methyl, n is 1 and alk is an optionally monomethylated ethylene radical.

3. The pharmaceutical composition of claim 1, wherein the active compound has the formula defined in claim 1, wherein R₁ is phenyl monosubstituted by methyl, methoxy, allyl, allyloxy, hydroxyl, acetylamino, propionyl, N-methyl-carbamoyl or chlorine, R₂ is hydrogen, R₃ is hydroxyl, R₄ is hydrogen and alk is ethylene.

4. The pharmaceutical composition of claim 1, wherein the active compound has the formula

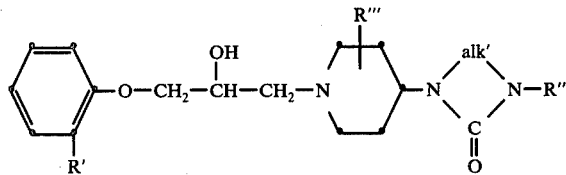

in which R' stands for halogen, lower alkyl or lower alkoxy, R" for lower alkyl or hydrogen, R'" for methyl or hydrogen and alk' for ethylene or an acid addition salt thereof.

5. The pharmaceutical composition of claim 1, wherein the active compound has the formula

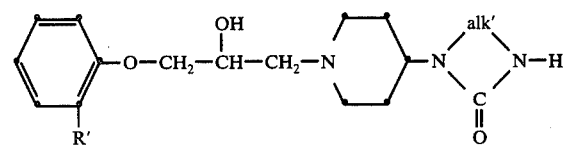

in which R' stands for lower alkyl or lower alkoxy and alk' for ethylene or an acid addition salt thereof.

6. The pharmaceutical composition of claim 1, wherein the active compound is 1-[3-(o-chlorophenoxy)-2-hydroxypropyl]-4-(2-oxo-1-imidazolidinyl)-piperidine or an acid addition salt thereof.

7. The pharmaceutical composition of claim 1, wherein the active compound is 1-[3-(o-methylphenoxy)-2-hydroxypropyl]-4-(2-oxo-1-imidazolidinyl)-piperidine or an acid addition salt thereof.

8. The pharmaceutical composition of claim 1, wherein the active compound is 1-[3-(o-methoxyphenoxy)-2-hydroxypropyl]-4-(2-oxo-1-imidazolidinyl)-piperidine or an acid addition salt thereof.

9. A pharmaceutical composition useful in treating hypertension and tachycardia which comprises a therapeutically effective amount of a piperidine compound defined in claim 1 and a therapeutically effective amount of an anti-hypertensive agent selected from the group consisting of α-amino-α-methyl-β-(3,4-dihydroxyphenyl)-propionic acid, β-amino-α-(3,4-dimethoxyphenyl)-propionic acid, 1,4-dihydrazinophthalazine, 1-hydrazinophthalazine, 2-[(N-p-tolyl)-N-(m-hydroxyphenyl)-aminomethyl]-imidazoline or β-(1-azacyclooctyl)-ethylguanidine.

10. The pharmaceutical composition as claimed in claim 9, containing 1-{1-[3-(o-methoxy-phenoxy)-2-hydroxy-1-propyl]-piperidyl-(4)}-imidazolidinone-(2) together with 1-α-amino-α-methyl-β-(3,4-dihydroxyphenyl)-propionic acid or β-(1-azacyclooctyl)-ethylguanidine sulphate.

11. A pharmaceutical composition useful in treating hypertension and tachycardia which comprises a therapeutically effective amount of a piperidine compound defined in claim 1 and a therapeutically effective amount of a diuretic selected from the group consisting of 6-chloro-7-sulphamyl-1,2,4-benzothiadiazine-1,1-dioxide, 6-trifluoromethyl-7-sulphamyl-1,2,4-benzothiadiazine-1,1-dioxide, 2-benzylthiomethyl-6-chloro-7-sulphamyl-1,2,4-benzothiadiazine-1,1-dioxide, 3-ethyl-6-chloro-7-sulphamyl-3,4-dihydro-1,2,4-benzothiadiazine-1,1-dioxide, 3-trichloromethyl-6-chloro-7-sulphamyl-3,4-dihydro-1,2,4-benzothiadiazine-1,1-dioxide, 3-benzyl-6-trifluoromethyl-7-sulphamyl-3,4-dihydro-1,2,4-benzothiadiazine-1,1-dioxide, 2-methyl-3-(2,2,2-trifluoroethylthiomethyl)-6-chloro-7-sulphamyl-3,4-dihydro-1,2,4-benzothiadiazine-1,1-dioxide, 3-(2,2,2-trifluoroethylthiomethyl)-6-chloro-7-sulphamyl-3,4-dihydro-1,2,4-benzothiadiazine-1,1-dioxide, 3-(5-norbornen-2-yl)-6-chloro-7-sulphamyl-3,4-dihydro-1,2,4-benzothiadiazine-1,1-dioxide, 2-methyl-3-chloromethyl-6-chloro-7-sulphamyl-3,4-dihydro-1,2,4-benzothiadiazine-1,1-dioxide, 6-chloro-7-sulphamyl-3,4-dihydro-1,2,4-benzothiadiazine-1,1-dioxide, 3-dichloromethyl-6-chloro-7-sulphamyl-3,4-dihydro-1,2,4-benzothiadiazine-1,1-dioxide, 3-cyclopentylmethyl-6-chloro-7-sulphamyl-3,4-dihydro-1,2,4-benzothiadiazine-1,1-dioxide, 6-trifluoromethyl-7-sulphamyl-3,4-dihydro-1,2,4-benzothiadiazine-1,1-dioxide and 3-isobutyl-6-chloro-7-sulphamyl-3,4-dihydro-1,2,4-benzothiadiazine-1,1-dioxide.

12. Pharmaceutical composition as claimed in claim 11, containing 1-{1-[3-(o-methoxy-phenoxy)-2-hydroxy-1-propyl]-piperidyl-(4)}-imidazolidinone-(2) together with 1-oxo-3-(3-sulphamyl-4-chloro-phenyl)-3-hydroxyisoindoline, 6-chloro-7-sulphamyl-3,4-dihydro-1,2,4-benzothiadiazine-1,1-dioxide, 3-cyclopentylmethyl-6-chloro-7-sulphamyl-3,4-dihydro-1,2,4-benzothiadiazine-1,1-dioxide or 5-(2-methylenebutyryl)-6-methyl-benzofurane2-carboxylic acid.

13. A method for the treatment of hypertension of tachycardia which comprises administering to a mammal afflicted therewith a pharmaceutical composition according to claim 1.

* * * * *